United States Patent
Scholl et al.

(10) Patent No.: US 11,155,935 B2
(45) Date of Patent: *Oct. 26, 2021

(54) METHOD FOR FORMING POROUS FIBERS

(71) Applicant: Kimberly-Clark Worldwide, Inc., Neenah, WI (US)

(72) Inventors: Neil T. Scholl, Neenah, WI (US); Vasily A. Topolkaraev, Appleton, WI (US); Antonio J. Carrillo Ojeda, Appleton, WI (US); Ryan J. McEneany, Appleton, WI (US); Theodore T. Tower, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 331 days.

This patent is subject to a terminal disclaimer.

(21) Appl. No.: 15/765,343

(22) PCT Filed: Dec. 9, 2016

(86) PCT No.: PCT/US2016/065826
§ 371 (c)(1),
(2) Date: Apr. 2, 2018

(87) PCT Pub. No.: WO2017/100570
PCT Pub. Date: Jun. 15, 2017

(65) Prior Publication Data
US 2018/0291528 A1    Oct. 11, 2018

Related U.S. Application Data

(60) Provisional application No. 62/266,122, filed on Dec. 11, 2015.

(51) Int. Cl.
*D01D 5/247* (2006.01)
*D04H 1/4326* (2012.01)
(Continued)

(52) U.S. Cl.
CPC ....... *D01D 5/247* (2013.01); *A61F 13/15658* (2013.01); *D01D 5/0885* (2013.01);
(Continued)

(58) Field of Classification Search
CPC .... D01F 6/00; D01F 8/00; D01D 1/00; D01D 1/70; D04H 1/40; D04H 3/00; D04H 3/14;
(Continued)

(56) References Cited

U.S. PATENT DOCUMENTS 3,423,255 A    1/1969  Joyce
3,802,817 A    4/1974  Matsuki et al.
(Continued)

FOREIGN PATENT DOCUMENTS

CN    103796744    *  9/2012    ............. B01D 63/02
EP    1550746         7/2005
(Continued)

OTHER PUBLICATIONS

Supplementary European Search Report for EP16873914 dated Jun. 19, 2019, 3 pages.
(Continued)

*Primary Examiner* — Matthew J Daniels
*Assistant Examiner* — Shibin Liang
(74) *Attorney, Agent, or Firm* — Dority & Manning, P.A.

(57) ABSTRACT

A method for forming porous fibers is provided. The fibers are formed from a thermoplastic composition containing a continuous phase, which includes a matrix polymer, and a nanoinclusion additive that is at least partially incompatible with the matrix polymer so that it becomes dispersed within the continuous phase as discrete nano-scale phase domains. The method generally includes traversing a bundle of the fibers over one or more draw bars that are in contact with a fluidic medium (e.g., water). In certain embodiments, for
(Continued)

example, the draw bar(s) are submerged in the fluidic medium. The fluidic medium is lower than the melting temperature of the matrix polymer.

21 Claims, 5 Drawing Sheets

(51) Int. Cl.
| | | |
|---|---|---|
| D04H 1/70 | (2012.01) | |
| D04H 3/009 | (2012.01) | |
| D04H 3/02 | (2006.01) | |
| D01D 5/098 | (2006.01) | |
| D01D 5/088 | (2006.01) | |
| D02J 1/22 | (2006.01) | |
| D01F 1/08 | (2006.01) | |
| D04H 1/4382 | (2012.01) | |
| A61F 13/15 | (2006.01) | |
| A61F 13/53 | (2006.01) | |

(52) U.S. Cl.
CPC ............ *D01D 5/098* (2013.01); *D01F 1/08* (2013.01); *D02J 1/223* (2013.01); *D04H 1/4326* (2013.01); *D04H 1/43828* (2020.05); *D04H 1/70* (2013.01); *D04H 3/009* (2013.01); *D04H 3/02* (2013.01); *A61F 2013/530233* (2013.01); *D04H 1/4383* (2020.05); *D04H 1/43832* (2020.05)

(58) Field of Classification Search
CPC ... D04H 4/30; D04H 7/30; B29D 7/00; D04C 5/16; D04C 5/18
See application file for complete search history.

(56) References Cited

U.S. PATENT DOCUMENTS

| | | | |
|---|---|---|---|
| 3,855,046 A | 12/1974 | Hansen et al. | |
| 3,932,571 A | 1/1976 | Dworjanyn | |
| 4,041,203 A | 8/1977 | Brock et al. | |
| 4,100,324 A | 7/1978 | Anderson et al. | |
| 4,374,888 A | 2/1983 | Bornslaeger | |
| 4,496,507 A * | 1/1985 | Okita | B29C 67/205 264/127 |
| 4,704,116 A | 11/1987 | Enloe | |
| 4,756,932 A * | 7/1988 | Puri | B01D 69/08 427/175 |
| 4,766,029 A | 8/1988 | Brock et al. | |
| 4,797,468 A | 1/1989 | De Vries | |
| 4,798,603 A | 1/1989 | Meyer et al. | |
| 4,937,299 A | 6/1990 | Ewen et al. | |
| D315,990 S | 4/1991 | Blenke et al. | |
| 5,169,706 A | 12/1992 | Collier, IV et al. | |
| 5,192,606 A | 3/1993 | Proxmire et al. | |
| 5,213,881 A | 5/1993 | Timmons et al. | |
| 5,218,071 A | 6/1993 | Tsutsui et al. | |
| 5,248,309 A | 9/1993 | Serbiak et al. | |
| 5,272,236 A | 12/1993 | Lai et al. | |
| 5,278,272 A | 1/1994 | Lai et al. | |
| 5,284,703 A | 2/1994 | Everhart et al. | |
| 5,322,728 A | 6/1994 | Davey et al. | |
| 5,350,624 A | 9/1994 | Georger et al. | |
| D358,035 S | 5/1995 | Zander et al. | |
| 5,464,688 A | 11/1995 | Timmons et al. | |
| 5,470,944 A | 11/1995 | Bonsignore | |
| 5,472,775 A | 12/1995 | Obijeski et al. | |
| 5,486,166 A | 1/1996 | Bishop et al. | |
| 5,490,846 A | 2/1996 | Ellis et al. | |
| 5,539,056 A | 7/1996 | Yang et al. | |
| 5,571,619 A | 11/1996 | McAlpin et al. | |
| 5,596,052 A | 1/1997 | Resconi et al. | |
| 5,620,779 A | 4/1997 | Levy et al. | |
| D384,508 S | 10/1997 | Zander et al. | |
| D384,819 S | 10/1997 | Zander et al. | |
| 5,702,377 A | 12/1997 | Collier, IV et al. | |
| D390,708 S | 2/1998 | Brown | |
| 5,770,682 A | 6/1998 | Ohara et al. | |
| 5,821,327 A | 10/1998 | Oota et al. | |
| 5,843,057 A | 12/1998 | McCormack | |
| 5,855,999 A | 1/1999 | McCormack | |
| 5,880,254 A | 3/1999 | Ohara et al. | |
| 5,931,823 A | 8/1999 | Stokes et al. | |
| 5,932,497 A | 8/1999 | Morman et al. | |
| 5,962,112 A | 10/1999 | Haynes et al. | |
| 5,997,981 A | 12/1999 | McCormack et al. | |
| 6,002,064 A | 12/1999 | Kobylivker et al. | |
| D418,305 S | 1/2000 | Zander et al. | |
| 6,015,764 A | 1/2000 | McCormack et al. | |
| 6,037,281 A | 3/2000 | Mathis et al. | |
| 6,060,638 A | 5/2000 | Paul et al. | |
| D428,267 S | 7/2000 | Romano, III et al. | |
| 6,090,325 A | 7/2000 | Wheat et al. | |
| 6,093,665 A | 7/2000 | Sayovitz et al. | |
| 6,111,163 A | 8/2000 | McCormack et al. | |
| 6,143,411 A * | 11/2000 | Ferguson | D01D 5/24 428/398 |
| 6,150,002 A | 11/2000 | Varona | |
| 6,326,458 B1 | 12/2001 | Gruber et al. | |
| 6,461,457 B1 | 10/2002 | Taylor et al. | |
| 6,500,563 B1 | 12/2002 | Datta et al. | |
| 6,642,429 B1 | 11/2003 | Carter et al. | |
| 6,663,611 B2 | 12/2003 | Blaney et al. | |
| 7,060,867 B2 | 6/2006 | Jameson | |
| 7,666,504 B2 * | 2/2010 | Ochi | B29C 48/40 428/398 |
| 7,718,747 B2 | 5/2010 | Alvares et al. | |
| 2004/0002273 A1 | 1/2004 | Fitting et al. | |
| 2005/0054255 A1 | 3/2005 | Morman et al. | |
| 2005/0059941 A1 | 3/2005 | Baldwin et al. | |
| 2005/0260911 A1 | 11/2005 | Ochi et al. | |
| 2014/0291887 A1 | 10/2014 | Coan et al. | |
| 2017/0362757 A1 | 12/2017 | Topolkaraev et al. | |
| 2018/0179668 A1* | 6/2018 | Topolkaraev | D01D 5/24 |

FOREIGN PATENT DOCUMENTS

| | | |
|---|---|---|
| EP | 2 716 798 A1 | 4/2014 |
| GB | 927586 | 5/1963 |
| KR | 20130030455 A | 3/2013 |
| KR | 101573817 B1 | 12/2015 |
| WO | WO 2004/061170 A1 | 7/2004 |
| WO | WO 2014/199269 A1 | 12/2014 |
| WO | WO2014199269 | 12/2014 |
| WO | WO 2015/036733 | 3/2015 |
| WO | WO2016094779 | 6/2016 |
| WO | WO 2017/100511 A1 | 6/2017 |

OTHER PUBLICATIONS

International Search Report and Written Opinion for PCT/US2016/065826 dated Mar. 28, 2017, 14 pages.

* cited by examiner

METHOD FOR FORMING POROUS FIBERS

RELATED APPLICATIONS

The present application is the national stage entry of International Patent Application No. PCT/US2016/065826 having a filing date of Dec. 9, 2016, which claims priority to U.S. provisional application Ser. No. 62/266,122, filed on Dec. 11, 2015, which are incorporated herein in their entirety by reference thereto.

BACKGROUND OF THE INVENTION

Significant efforts have been made to produce low density fibers to improve the use of natural resources and reduction of the carbon footprint in finished products. A typical approach to producing low density fibers is by foaming the polymer using physical or chemical blowing agents, which create gas cells though the bulk. Chemical blowing agents are compounds that undergo chemical reaction that liberates gas and creates the cellular structure through the bulk of the polymer. Physical blowing agents are typically compressed gases that are dispersed in the polymer and expand creating the cells. Regardless, typical foaming processes induce low molecular orientation because the cell formation happens when the polymer is in the molten state. This prevents the polymer from strain hardening, which typically occurs at temperatures well above the melting temperature or glass transition temperature of the polymer, yielding products with low mechanical strength. Furthermore, typical foaming processes generate large cell sizes, such as greater than 100 μm. This reduces the melt strength, thus leading to breaks in a fiber during spinning. As such, a need currently exists for an improved technique in creating a porous structure in polyolefin fibers so that they can possess a lower density.

SUMMARY OF THE INVENTION

In accordance with one embodiment of the present invention, a method for forming porous fibers is disclosed. The method comprises supplying a bundle of fibers to a drawing system that includes at least one draw bar in contact with a fluidic medium having a temperature that is lower than the melting temperature of the matrix polymer. At least a portion of the fibers are formed from a thermoplastic composition containing a continuous phase that includes a matrix polymer and a nanoinclusion additive dispersed within the continuous phase in the form of discrete domains. The bundle of fibers is traversed over the draw bar, thereby forming a porous network in the fibers that includes a plurality of nanopores.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Figure 1:
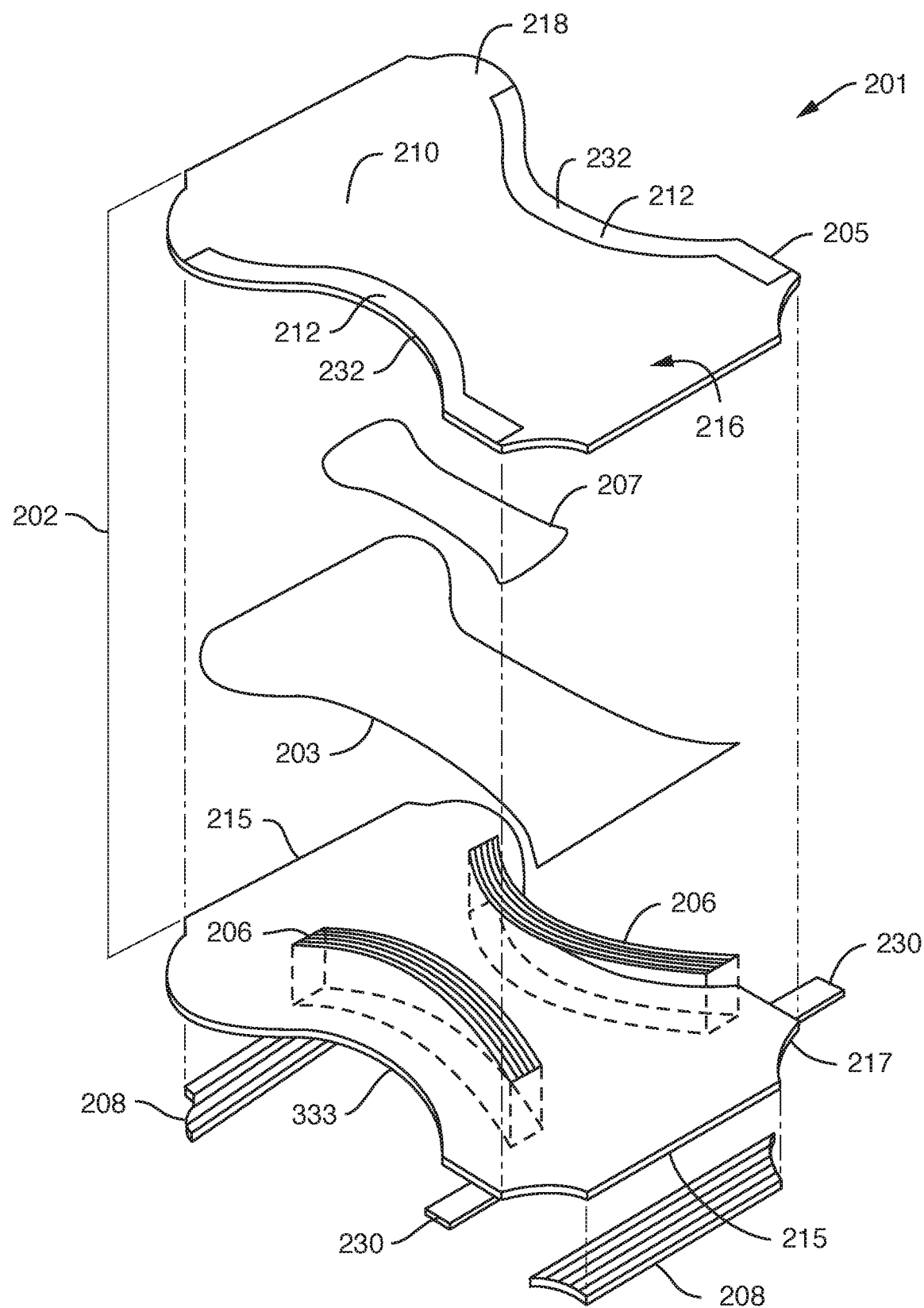
FIG. 1 is a perspective view of one embodiment of the absorbent article that may employ the fibers of the present invention.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a method for forming porous fibers. The fibers are formed from a thermoplastic composition containing a continuous phase, which includes a matrix polymer, and a nanoinclusion additive that is at least partially incompatible with the matrix polymer so that it becomes dispersed within the continuous phase as discrete nano-scale phase domains. The method of the present invention generally includes traversing a bundle of the fibers over one or more draw bars that are in contact with a fluidic medium (e.g., water). In certain embodiments, for example, the draw bar(s) are submerged in the fluidic medium. The fluidic medium is lower than the melting temperature of the matrix polymer, such as at least about 10° C., in some embodiments at least about 20° C., and in some embodiments, at least about 30° C. below the melting temperature. For example, the temperature of the fluidic medium is typically from about −20° C. to about 90° C., in some embodiments from about −10° C. to about 60° C., and in some embodiments, from about 0° C. to about 45° C.

When drawn in this manner, it is believed that the nano-scale phase domains within the fibers are able to interact in a unique manner to create a network of pores in the interior wall of the fibers. Namely, it is believed that elongational strain experienced during drawing can initiate intensive localized shear zones and/or stress intensity zones (e.g., normal stresses) near the discrete phase domains as a result of stress concentrations that arise from the incompatibility of the materials. These shear and/or stress intensity zones cause some initial debonding in the matrix polymer adjacent to the domains. Once initial pores are formed, the matrix located between domains can deform plastically to create internal stretched areas that locally narrow (or neck) and strain-harden. This process allows the formation of pores through the bulk of the interior wall that grow in the stretching direction, thereby leading to the formation of a porous network while the molecular orientation leads to strain-hardening that enhances mechanical strength. In addition to simply forming a porous network, the present inventors have also discovered that the drawing process can also reduce the frequency of necks in the fibers and thus increase the overall void volume. More particularly, it is believed that as the fibers exit the draw bar(s), frictional forces are released and the fibers can experience stress and strain, which helps localize deformation and reduce number of neck points that are generated. In addition, the low temperature fluidic medium can effectively function as a "heat sink" in that it can absorb heat generated by plastic flow of the fibers at low temperatures. Among other things, the ability to remove heat from the fibers during drawing can help keep the fibers rigid before and after drawing, which makes it less likely that they will undergo deformation. This stabilizes the porous network by decreasing the likelihood that multiple necks will be formed.

Various embodiments of the present invention will now be described in more detail.

I. Thermoplastic Composition

A. Matrix Polymer

The matrix polymers typically constitute from about 60 wt. % to about 99 wt. %, in some embodiments from about 60 wt. % to about 98 wt. %, and in some embodiments, from about 80 wt. % to about 95 wt. % of the thermoplastic composition.

The nature of the matrix polymer(s) used to form the continuous phase is not critical and any suitable polymer may generally be employed, such as polyesters (e.g., polyethylene terephthalate, polylactic acid, etc.), polyolefins, styrenic polymers, polyamides, etc.

In one embodiment, for instance, a polyolefin may be employed that has a melting temperature of from about 100° C. to about 220° C., in some embodiments from about 120° C. to about 200° C., and in some embodiments, from about 140° C. to about 180° C. The melting temperature may be determined using differential scanning calorimetry ("DSC") in accordance with ASTM D-3417. Suitable polyolefins may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, and so forth. In one particular embodiment, the polymer is a propylene polymer, such as homopolypropylene or a copolymer of propylene. The propylene polymer may, for instance, be formed from a substantially isotactic polypropylene homopolymer or a copolymer containing equal to or less than about 10 wt. % of other monomers, i.e., at least about 90% by weight propylene. Such homopolymers may have a melting point of from about 140° C. to about 170° C.

Of course, other polyolefins may also be employed in the composition of the present invention. In one embodiment, for example, the polyolefin may be a copolymer of ethylene or propylene with another α-olefin, such as a $C_3$-$C_{20}$ α-olefin or $C_3$-$C_{12}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Exemplary olefin copolymers for use in the present invention include ethylene-based copolymers available under the designation EXACT™ from ExxonMobil Chemical Company of Houston, Tex. Other suitable ethylene copolymers are available under the designation ENGAGE™ AFFINITY™, DOWLEX™ (LLDPE) and ATTANE™ (ULDPE) from Dow Chemical Company of Midland, Mich. Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al. Suitable propylene copolymers are also commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Suitable polypropylene homopolymers may include Exxon Mobil 3155 polypropylene, Exxon Mobil Achieve™ resins, and Total M3661 PP resin. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al.

Any of a variety of known techniques may generally be employed to form the olefin copolymers. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obreski et al.; U.S. Pat. No. 5,272,236 to Lai et al.; and U.S. Pat. No. 6,090,325 to Wheat, et al. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

B. Nanoinclusion Additive

As used herein, the term "nanoinclusion additive" generally refers to a material that is capable of being dispersed within the polymer matrix in the form of discrete domains of a nano-scale size. For example, prior to drawing, the domains may have an average cross-sectional dimension of from about 1 to about 1000 nanometers, in some embodiments from about 5 to about 800 nanometers, in some embodiments from about 10 to about 500 nanometers, and in some embodiments from about 20 to about 200 nanometers. The domains may have a variety of different shapes, such as elliptical, spherical, cylindrical, plate-like, tubular, etc. In one embodiment, for example, the domains have a substantially elliptical shape. The nanoinclusion additive is typically employed in an amount of from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase matrix. The concentration of the nanoinclusion additive in the entire thermoplastic composition may likewise be from about 0.01 wt. % to about 15 wt. %, in some embodiments from about 0.05 wt. % to about 10 wt. %, and in some embodiments, from about 0.3 wt. % to about 6 wt. % of the thermoplastic composition.

The nanoinclusion additive is partially incompatible with the matrix polymer in the sense that it can be substantially uniformly distributed within the matrix polymer, but in the form of discrete domains. Such partial incompatibility can be accomplished in a variety of ways. In certain embodiments, for example, the nanoinclusion additive may possess a nonpolar component (e.g., olefin) that is compatible with the matrix polymer and allows it to become uniformly distributed therein. Nevertheless, the additive may also include a polar component that is incompatible with the matrix polymer, thereby allowing it to coalesce or segregate into discrete domains. Such a component may include low or high molecular weight polar molecular segments or blocks, ionic groups, charged or uncharged polar domains, and/or polar molecular groups. Alternatively, the additive may be entirely nonpolar in nature, but possess certain physical properties that still allow for discrete domains to be formed. For example, in certain embodiments, the nanoinclusion additive may be compatible or miscible with the matrix polymer above a certain temperature, but phase separate at temperatures lower than the critical solution temperature. In this manner, the nanoinclusion additive can form a stable blend with the matrix polymer in the melt phase, but as the temperature decreases, the continuous phase crystallizes and segregates so that the nanoinclusion additive can phase separate, coalesce, and form separate nano-scale domains.

The particular state or form of the nanoinclusion additive is not critical so long as the desired domains can be formed. For example, in some embodiments, the nanoinclusion additive can be in the form of a liquid or semi-solid at room temperature (e.g., 25° C.). Such a liquid can be readily dispersed in the matrix to form a metastable dispersion, and then quenched to preserve the domain size by reducing the temperature of the blend. The kinematic viscosity of such a liquid or semi-solid material is typically from about 0.7 to about 200 centistokes ("cs"), in some embodiments from about 1 to about 100 cs, and in some embodiments, from about 1.5 to about 80 cs, determined at 40° C. Suitable liquids or semi-solids may include, for instance, silicones, silicone-polyether copolymers, aliphatic polyesters, aromatic polyesters, alkylene glycols (e.g., ethylene glycol, diethylene glycol, triethylene glycol, tetraethylene glycol, propylene glycol, polyethylene glycol, polypropylene glycol, polybutylene glycol, etc.), alkane diols (e.g., 1,3-propanediol, 2,2-dimethyl-1,3-propanediol, 1,3-butanediol, 1,4-butanediol, 1,5-pentanediol, 1,6-hexanediol, 2,2,4-trimethyl-1,6 hexanediol, 1,3-cyclohexanedimethanol, 1,4-cyclohexanedimethanol, 2,2,4,4-tetramethyl-1,3-cyclobutanediol, etc.), amine oxides (e.g., octyldimethylamine oxide), fatty acid esters, fatty acid amides (e.g., oleamide, erucamide, stearamide, ethylene bis(stearamide), etc.), mineral, and vegetable oils, and so forth. One particularly suitable liquid or semi-solid is polyether polyol, such as commercially available under the trade name Pluriol® WI from BASF Corp.

In yet other embodiments, the nanoinclusion additive is in the form of a solid, which may be amorphous, crystalline, or semi-crystalline. For example, the nanoinclusion additive may be polymeric in nature and possess a relatively high molecular weight to help improve the melt strength and stability of the thermoplastic composition. As indicated above, the nanoinclusion additive is partially incompatible with the matrix polymer. One example of such an additive is a microcrystalline polyolefin wax, which is typically derived from ethylene and/or $C_3$-$C_{10}$-alk-1-enes, such as from propylene, 1-butene, 1-pentene, 1-hexene, 1-heptene, 1-octene, 1-nonene, and 1-decene. Microcrystalline waxes typically have a relatively low melting temperature, such as from about 30° C. to about 150° C., in some embodiments from about 50° C. to about 140° C., and in some embodiments, from about 80° C. to about 130° C. At such low melting temperatures, the wax can form a miscible blend with the matrix polymer when in the melt phase, but as the temperature decreases and polymer crystalizes or solidifies, the wax will segregate and coalesce forming separate nano-scale domains.

Another example of a polymeric nanoinclusion additive is a functionalized polyolefin that contains a polar and non-polar component. The polar component may, for example, be provided by one or more functional groups and the nonpolar component may be provided by an olefin. The olefin component of the nanoinclusion additive may generally be formed from any linear or branched α-olefin monomer, oligomer, or polymer (including copolymers) derived from an olefin monomer, such as described above. The functional group of the nanoinclusion additive may be any group, molecular segment and/or block that provides a polar component to the molecule and is not compatible with the matrix polymer. Examples of molecular segment and/or blocks not compatible with polyolefin may include acrylates, styrenics, polyesters, polyamides, etc. The functional group can have an ionic nature and comprise charged metal ions. Particularly suitable functional groups are maleic anhydride, maleic acid, fumaric acid, maleimide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond®, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation Polybond®, Eastman Chemical Company under the designation Eastman G series, and Arkema under the designation Orevac®.

In certain embodiments, the polymeric nanoinclusion additive may also be reactive. One example of such a reactive nanoinclusion additive is a polyepoxide that contains, on average, at least two oxirane rings per molecule. Without intending to be limited by theory, it is believed that such polyepoxide molecules can undergo a reaction (e.g., chain extension, side chain branching, grafting, copolymer formation, etc.) with certain components of the composition to improve melt strength without significantly reducing glass transition temperature. The reactive additive can also provide compatibilization between the matrix polymer and other more polar additives, such as microinclusion additives, and can improve the uniformity of dispersion and reduce the size of microinclusion additives. For example, as will be described in more detail below, certain embodiments of the present invention may employ a polyester as a microinclusion additive. In such embodiments, the reactive nanoinclusion additive may enable a nucleophilic ring-opening reaction via a carboxyl terminal group of the polyester (esterification) or via a hydroxyl group (etherification). Oxazoline side reactions may likewise occur to form esteramide moieties. Through such reactions, the molecular weight of a polyester microinclusion additive may be increased to counteract the degradation often observed during melt processing. The present inventors have discovered that too much of a reaction can lead to crosslinking between polymer backbones. If such crosslinking is allowed to proceed to a significant extent, the resulting polymer blend can become brittle and difficult to process into a fiber with the desired strength and elongation properties.

In this regard, the present inventors have discovered that polyepoxides having a relatively low epoxy functionality may be particularly effective, which may be quantified by its "epoxy equivalent weight." The epoxy equivalent weight reflects the amount of resin that contains one molecule of an epoxy group, and it may be calculated by dividing the number average molecular weight of the modifier by the number of epoxy groups in the molecule. The polyepoxide of the present invention typically has a number average molecular weight from about 7,500 to about 250,000 grams per mole, in some embodiments from about 15,000 to about 150,000 grams per mole, and in some embodiments, from about 20,000 to 100,000 grams per mole, with a polydispersity index typically ranging from 2.5 to 7. The polyepoxide may contain less than 50, in some embodiments from 5 to 45, and in some embodiments, from 15 to 40 epoxy groups. In turn, the epoxy equivalent weight may be less than about 15,000 grams per mole, in some embodiments from about 200 to about 10,000 grams per mole, and in some embodiments, from about 500 to about 7,000 grams per mole.

The polyepoxide may be a linear or branched, homopolymer or copolymer (e.g., random, graft, block, etc.) containing terminal epoxy groups, skeletal oxirane units, and/or pendent epoxy groups. The monomers employed to form such polyepoxides may vary. In one particular embodiment, for example, the polyepoxide contains at least one epoxy-functional (meth)acrylic monomeric component. As used herein, the term "(meth)acrylic" includes acrylic and methacrylic monomers, as well as salts or esters thereof, such as acrylate and methacrylate monomers. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate.

The polyepoxide typically has a relatively high molecular weight, as indicated above, so that it may not only result in chain extension, but also help to achieve the desired blend morphology. The resulting melt flow rate of the polymer is thus typically within a range of from about 10 to about 200 grams per 10 minutes, in some embodiments from about 40 to about 150 grams per 10 minutes, and in some embodiments, from about 60 to about 120 grams per 10 minutes, determined at a load of 2160 grams and at a temperature of 190° C.

The polyepoxide also typically includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene. Another suitable monomer may include a (meth)acrylic monomer that is not epoxy-functional. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof.

In one particularly desirable embodiment of the present invention, the polyepoxide is a terpolymer formed from an epoxy-functional (meth)acrylic monomeric component, α-olefin monomeric component, and non-epoxy functional (meth)acrylic monomeric component. For example, the polyepoxide may be poly(ethylene-co-methylacrylate-co-glycidyl methacrylate), which has the following structure:

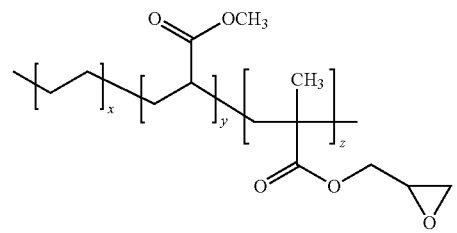

wherein, x, y, and z are 1 or greater.

The epoxy functional monomer may be formed into a polymer using a variety of known techniques. For example, a monomer containing polar functional groups may be grafted onto a polymer backbone to form a graft copolymer. Such grafting techniques are well known in the art and described, for instance, in U.S. Pat. No. 5,179,164. In other embodiments, a monomer containing epoxy functional groups may be copolymerized with a monomer to form a block or random copolymer using known free radical polymerization techniques, such as high pressure reactions, Ziegler-Natta catalyst reaction systems, single site catalyst (e.g., metallocene) reaction systems, etc.

The relative portion of the monomeric component(s) may be selected to achieve a balance between epoxy-reactivity and melt flow rate. More particularly, high epoxy monomer contents can result in good reactivity, but too high of a content may reduce the melt flow rate to such an extent that the polyepoxide adversely impacts the melt strength of the polymer blend. Thus, in most embodiments, the epoxy-functional (meth)acrylic monomer(s) constitute from about 1 wt. % to about 25 wt. %, in some embodiments from about 2 wt. % to about 20 wt. %, and in some embodiments, from about 4 wt. % to about 15 wt. % of the copolymer. The α-olefin monomer(s) may likewise constitute from about 55 wt. % to about 95 wt. %, in some embodiments from about 60 wt. % to about 90 wt. %, and in some embodiments, from about 65 wt. % to about 85 wt. % of the copolymer. When employed, other monomeric components (e.g., non-epoxy functional (meth)acrylic monomers) may constitute from about 5 wt. % to about 35 wt. %, in some embodiments from about 8 wt. % to about 30 wt. %, and in some embodiments, from about 10 wt. % to about 25 wt. % of the copolymer. One specific example of a suitable polyepoxide that may be used in the present invention is commercially available from Arkema under the name LOTADER® AX8950 or AX8900. LOTADER® AX8950, for instance, has a melt flow rate of 70 to 100 g/10 min and has a glycidyl methacrylate monomer content of 7 wt. % to 11 wt. %, a methyl acrylate monomer content of 13 wt. % to 17 wt. %, and an ethylene monomer content of 72 wt. % to 80 wt. %. Another suitable polyepoxide is commercially available from DuPont under the name ELVALOY® PTW, which is a terpolymer of ethylene, butyl acrylate, and glycidyl methacrylate and has a melt flow rate of 12 g/10 min.

In addition to controlling the type and relative content of the monomers used to form the polyepoxide, the overall weight percentage may also be controlled to achieve the desired benefits. For example, if the modification level is too low, the desired increase in melt strength and mechanical properties may not be achieved. The present inventors have also discovered, however, that if the modification level is too high, processing may be restricted due to strong molecular interactions (e.g., crosslinking) and physical network formation by the epoxy functional groups. Thus, the polyepoxide is typically employed in an amount of from about 0.05 wt. % to about 10 wt. %, in some embodiments from about 0.1 wt. % to about 8 wt. %, in some embodiments from about 0.5 wt. % to about 5 wt. %, and in some embodiments, from about 1 wt. % to about 3 wt. %, based on the weight of the matrix polymers employed in the composition. The polyepoxide may also constitute from about 0.05 wt. % to about 10 wt. %, in some embodiments from about 0.05 wt. % to about 8 wt. %, in some embodiments from about 0.1 wt. % to about 5 wt. %, and in some embodiments, from about 0.5 wt. % to about 3 wt. %, based on the total weight of the composition.

Other reactive nanoinclusion additives may also be employed in the present invention, such as oxazoline-functionalized polymers, cyanide-functionalized polymers, etc. When employed, such reactive nanoinclusion additives may be employed within the concentrations noted above for the polyepoxide. In one particular embodiment, an oxazoline-grafted polyolefin may be employed that is a polyolefin grafted with an oxazoline ring-containing monomer. The oxazoline may include a 2-oxazoline, such as 2-vinyl-2-oxazoline (e.g., 2-isopropenyl-2-oxazoline), 2-fatty-alkyl-2-oxazoline (e.g., obtainable from the ethanolamide of oleic acid, linoleic acid, palmitoleic acid, gadoleic acid, erucic acid and/or arachidonic acid) and combinations thereof. In another embodiment, the oxazoline may be selected from ricinoloxazoline maleinate, undecyl-2-oxazoline, soya-2-oxazoline, ricinus-2-oxazoline and combinations thereof, for example. In yet another embodiment, the oxazoline is selected from 2-isopropenyl-2-oxazoline, 2-isopropenyl-4,4-dimethyl-2-oxazoline and combinations thereof.

In certain embodiments of the present invention, multiple nanoinclusion additives may be employed in combination. For instance, a first nanoinclusion additive (e.g., polyepoxide) may be dispersed in the form of domains having an average cross-sectional dimension of from about 50 to about 500 nanometers, in some embodiments from about 60 to about 400 nanometers, and in some embodiments from about 80 to about 300 nanometers. A second nanoinclusion additive may also be dispersed in the form of domains that are smaller than the first nanoinclusive additive, such as those having an average cross-sectional dimension of from about 1 to about 50 nanometers, in some embodiments from about 2 to about 45 nanometers, and in some embodiments from about 5 to about 40 nanometers. When employed, the first and/or second nanoinclusion additives typically constitute from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase (matrix polymer(s)). The concentration of the first and/or second nanonclusion additives in the entire thermoplastic composition may likewise be from about 0.01 wt. % to about 15 wt. %, in some embodiments from about 0.05 wt. % to about 10 wt. %, and in some embodiments, from about 0.1 wt. % to about 8 wt. % of the thermoplastic composition.

Nanofillers may optionally be employed for the second nanoinclusion additive, examples of which may include carbon black, carbon nanotubes, carbon nanofibers, nanoclays, metal nanoparticles, nanosilica, nanoalumina, etc. Nanoclays are particularly suitable. The term "nanoclay" generally refers to nanoparticles of a clay material (a naturally occurring mineral, an organically modified mineral, or a synthetic nanomaterial), which typically have a platelet structure. Examples of nanoclays include, for instance, montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc. An example of a suitable nanoclay is Cloisite®, which is a montmorillonite nanoclay and commercially available from Southern Clay Products, Inc. Other examples of synthetic nanoclays include but are not limited to a mixed-metal hydroxide nanoclay, layered double hydroxide nanoclay (e.g., sepiocite), laponite, hectorite, saponite, indonite, etc.

If desired, the nanoclay may contain a surface treatment to help improve compatibility with the matrix polymer (e.g., polyester). The surface treatment may be organic or inorganic. In one embodiment, an organic surface treatment is employed that is obtained by reacting an organic cation with the clay. Suitable organic cations may include, for instance, organoquaternary ammonium compounds that are capable of exchanging cations with the clay, such as dimethyl bis[hydrogenated tallow] ammonium chloride (2M2HT), methyl benzyl bis[hydrogenated tallow] ammonium chloride (MB2HT), methyl tris[hydrogenated tallow alkyl] chloride (M3HT), etc. Examples of commercially available organic nanoclays may include, for instance, Dellite® 43B (Laviosa Chimica of Livorno, Italy), which is a montmorillonite clay modified with dimethyl benzylhydrogenated tallow ammonium salt. Other examples include Cloisite® 25A and Cloisite® 30B (Southern Clay Products) and Nanofil 919 (SW Chemie). If desired, the nanofiller can be blended with a carrier resin to form a masterbatch that enhances the compatibility of the additive with the other polymers in the composition. Particularly suitable carrier resins include, for instance, polyesters (e.g., polylactic acid, polyethylene terephthalate, etc.); polyolefins (e.g., ethylene polymers, propylene polymers, etc.); and so forth, as described in more detail above.

Regardless of the material employed, the nanoinclusion additive is typically selected to have a certain viscosity (or melt flow rate) to ensure that the discrete domains and resulting pores can be adequately maintained. For example, if the viscosity of the nanoinclusion additive is too low (or melt flow rate is too high), it tends to flow and disperse uncontrollably through the continuous phase. This results in lamellar, plate-like domains or co-continuous phase structures that are difficult to maintain and also likely to prematurely fracture. Conversely, if the viscosity is too high (or melt flow rate is too low), it tends to clump together and form very large elliptical domains, which are difficult to disperse during blending. This may cause uneven distribution of the nanoinclusion additive through the entirety of the continuous phase. For instance, the ratio of the melt flow rate of the polyolefin to the melt flow rate of a polymeric nanoinclusion additive, for instance, may be from about 0.2 to about 8, in some embodiments from about 0.5 to about 6, and in some embodiments, from about 1 to about 5. The nanoinclusion additive may, for example, have a melt flow rate (on a dry basis) of from about 0.1 to about 100 grams per 10 minutes, in some embodiments from about 0.5 to about 50 grams per 10 minutes, and in some embodiments, from about 5 to about 15 grams per 10 minutes, determined at a load of 2160 grams and at a temperature at least about 40° C. above the melting temperature (e.g., at 190° C.) in accordance with ASTM D1238. The polyolefin may likewise have a melt flow rate (on a dry basis) of from about 0.5 to about 80 grams per 10 minutes, in some embodiments from about 1 to about 40 grams per 10 minutes, and in some embodiments, from about 5 to about 20 grams per 10 minutes, determined at a load of 2160 grams and at a temperature at least about 40° C. above the melting temperature (e.g., at 230° C.) in accordance with ASTM D1238.

C. Microinclusion Additive

Although not required, the composition of the present invention may also employ a microinclusion additive. As used herein, the term "microinclusion additive" generally refers to any material that is capable of being dispersed within the polymer matrix in the form of discrete domains of a micro-scale size. For example, prior to drawing, the domains may have an average cross-sectional dimension of from about 0.1 μm to about 25 μm, in some embodiments from about 0.5 μm to about 20 μm, and in some embodiments from about 1 μm to about 10 μm. When employed, the present inventors have discovered that the micro-scale and nano-scale phase domains are able to interact in a unique manner when subjected to a deformation and elongational strain (e.g., drawing) to create a network of pores. Namely, it is believed that elongational strain can initiate intensive localized shear zones and/or stress intensity zones (e.g., normal stresses) near the micro-scale discrete phase domains as a result of stress concentrations that arise from the incompatibility of the materials. These shear and/or stress intensity zones cause some initial debonding in the matrix polymer adjacent to the micro-scale domains. Notably, however, the localized shear and/or stress intensity zones created near the nano-scale discrete phase domains may overlap with the micro-scale zones to cause even further debonding to occur in the polymer matrix, thereby creating a substantial number of nanopores adjacent to the nano-scale domains and/or micro-scale domains.

The particular nature of the microinclusion additive is not critical, and may include liquids, semi-solids, or solids (e.g., amorphous, crystalline, or semi-crystalline). In certain embodiments, the microinclusion additive is polymeric in nature and possesses a relatively high molecular weight to help improve the melt strength and stability of the thermoplastic composition. Typically, the microinclusion additive polymer may be generally incompatible with the matrix polymer. In this manner, the additive can better become dispersed as discrete phase domains within a continuous phase of the matrix polymer. The discrete domains are capable of absorbing energy that arises from an external force, which increases the overall toughness and strength of the resulting fiber. The domains may have a variety of different shapes, such as elliptical, spherical, cylindrical, plate-like, tubular, etc. In one embodiment, for example, the domains have a substantially elliptical shape. The physical dimension of an individual domain is typically small enough to minimize the propagation of cracks through the fiber upon the application of an external stress, but large enough to initiate microscopic plastic deformation and allow for shear zones at and around particle inclusions.

The microinclusion additive may have a certain melt flow rate (or viscosity) to ensure that the discrete domains and resulting pores can be adequately maintained. For example, if the melt flow rate of the additive is too high, it tends to flow and disperse uncontrollably through the continuous phase. This results in lamellar, plate-like domains or co-continuous phase structures that are difficult to maintain and also likely to prematurely fracture. Conversely, if the melt flow rate of the additive is too low, it tends to clump together and form very large elliptical domains, which are difficult to disperse during blending. This may cause uneven distribution of the additive through the entirety of the continuous phase. In this regard, the present inventors have discovered that the ratio of the melt flow rate of the microinclusion additive to the melt flow rate of the matrix polymer is typically from about 0.5 to about 10, in some embodiments from about 1 to about 8, and in some embodiments, from about 2 to about 6. The microinclusion additive may, for example, have a melt flow rate of from about 5 to about 200 grams per 10 minutes, in some embodiments from about 20 to about 150 grams per 10 minutes, and in some embodiments, from about 40 to about 100 grams per 10 minutes, determined at a load of 2160 grams and at a temperature at least about 40° C. above its melting temperature (e.g., 210° C.).

In addition to the properties noted above, the mechanical characteristics of the microinclusion additive may also be selected to achieve the desired porous network. For example, applied with an external force, stress concentrations (e.g., including normal or shear stresses) and shear and/or plastic yielding zones may be initiated at and around the discrete phase domains as a result of stress concentrations that arise from a difference in the elastic modulus of the additive and matrix polymer. Larger stress concentrations promote more intensive localized plastic flow at the domains, which allows them to become significantly elongated when stresses are imparted. These elongated domains can allow the composition to exhibit a more pliable and softer behavior. To enhance the stress concentrations, the microinclusion additive may be selected to have a relatively high Young's modulus of elasticity in comparison to the matrix polymer. For example, the ratio of the modulus of elasticity of the additive to that of matrix polymer is typically from about 1 to about 250, in some embodiments from about 2 to about 100, and in some embodiments, from about 2 to about 50. The modulus of elasticity of the microinclusion additive may, for instance, range from about 200 to about 3,500 Megapascals (MPa), in some embodiments from about 300 to about 2,000 MPa, and in some embodiments, from about 400 to about 1,500 MPa. To the contrary, the modulus of elasticity of the polyolefin may, for instance, range from about 100 to about 1,500 MPa, and in some embodiments, from about 200 to about 1000 MPa. Alternatively, the modulus of elasticity of microinclusion additive can be lower than the modulus of elasticity of matrix polymer. The modulus of elasticity may, for example, range from about 10 MPa to about 100 MPa, and optionally from about 20 MPA to about 80 MPa.

While a wide variety of microinclusion additives may be employed that have the properties identified above, particularly suitable examples of such additives may include styrenic copolymers (e.g., styrene-butadiene-styrene, styrene-isoprene-styrene, styrene-ethylene-propylene-styrene, styrene-ethylene-butadiene-styrene, etc.); fluoropolymers, such as polyvinyl chloride (PVC), polytetrafluoroethylene (PTFE), polychlorotrifluoroethylene (PCTFE), etc.; polyvinyl alcohols; polyvinyl acetates; polyesters, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.), aliphatic-aromatic copolyesters (e.g., polybutylene adipate terephthalate, polyethylene adipate terephthalate, polyethylene adipate isophthalate, polybutylene adipate isophthalate, etc.), aromatic polyesters (e.g., polyethylene terephthalate, polybutylene terephthalate, etc.); and so forth.

Particularly suitable are microinclusion additives that are generally rigid in nature to the extent that they have a relatively high glass transition temperature. For example, the glass transition temperature ("$T_g$") may be about 0° C. or more, in some embodiments from about 5° C. to about 100° C., in some embodiments from about 30° C. to about 80° C., and in some embodiments, from about 50° C. to about 75° C. The glass transition temperature may be determined by dynamic mechanical analysis in accordance with ASTM E1640-09.

One particularly suitable rigid polyester is polylactic acid, which may generally be derived from monomer units of any isomer of lactic acid, such as levorotory-lactic acid ("L-lactic acid"), dextrorotatory-lactic acid ("D-lactic acid"), meso-lactic acid, or mixtures thereof. Monomer units may also be formed from anhydrides of any isomer of lactic acid, including L-lactide, D-lactide, meso-lactide, or mixtures thereof. Cyclic dimers of such lactic acids and/or lactides may also be employed. Any known polymerization method, such as polycondensation or ring-opening polymerization, may be used to polymerize lactic acid. A small amount of a chain-extending agent (e.g., a diisocyanate compound, an epoxy compound or an acid anhydride) may also be employed. The polylactic acid may be a homopolymer or a copolymer, such as one that contains monomer units derived from L-lactic acid and monomer units derived from D-lactic acid. Although not required, the rate of content of one of the monomer unit derived from L-lactic acid and the monomer unit derived from D-lactic acid is preferably about 85 mole % or more, in some embodiments about 90 mole % or more, and in some embodiments, about 95 mole % or more. Multiple polylactic acids, each having a different ratio between the monomer unit derived from L-lactic acid and the monomer unit derived from D-lactic acid, may be blended at an arbitrary percentage. Of course, polylactic acid may also be blended with other types of polymers (e.g., polyolefins, polyesters, etc.).

In one particular embodiment, the polylactic acid has the following general structure:

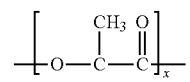

One specific example of a suitable polylactic acid polymer that may be used in the present invention is commercially available from Biomer, Inc. of Krailling, Germany) under the name BIOMER™ L9000. Other suitable polylactic acid polymers are commercially available from Natureworks LLC of Minnetonka, Minn. (NATUREWORKS®) or Mitsui Chemical (LACEA™). Still other suitable polylactic acids may be described in U.S. Pat. Nos. 4,797,468; 5,470,944; 5,770,682; 5,821,327; 5,880,254; and 6,326,458, which are incorporated herein in their entirety by reference thereto for all purposes.

The polylactic acid typically has a number average molecular weight ("$M_n$") ranging from about 40,000 to about 180,000 grams per mole, in some embodiments from about 50,000 to about 160,000 grams per mole, and in some embodiments, from about 80,000 to about 120,000 grams per mole. Likewise, the polymer also typically has a weight average molecular weight ("$M_w$") ranging from about 80,000 to about 250,000 grams per mole, in some embodiments from about 100,000 to about 200,000 grams per mole, and in some embodiments, from about 110,000 to about 160,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art.

Some types of neat polyesters (e.g., polylactic acid) can absorb water from the ambient environment such that it has a moisture content of about 500 to 600 parts per million ("ppm"), or even greater, based on the dry weight of the starting polylactic acid. Moisture content may be determined in a variety of ways as is known in the art, such as in accordance with ASTM D 7191-05, such as described below. Because the presence of water during melt processing can hydrolytically degrade the polyester and reduce its molecular weight, it is sometimes desired to dry the polyester prior to blending. In most embodiments, for example, it is desired that the renewable polyester have a moisture content of about 300 parts per million ("ppm") or less, in some embodiments about 200 ppm or less, in some embodiments from about 1 to about 100 ppm prior to blending with the microinclusion additive. Drying of the polyester may occur, for instance, at a temperature of from about 50° C. to about 100° C., and in some embodiments, from about 70° C. to about 80° C.

Regardless of the materials employed, the relative percentage of the microinclusion additive in the thermoplastic composition is selected to achieve the desired properties without significantly impacting the resulting composition. For example, the microinclusion additive is typically employed in an amount of from about 1 wt. % to about 30 wt. %, in some embodiments from about 2 wt. % to about 25 wt. %, and in some embodiments, from about 5 wt. % to about 20 wt. % of the thermoplastic composition, based on the weight of the matrix polymer employed in the composition. The concentration of the microinclusion additive in the entire thermoplastic composition may likewise constitute from about 0.1 wt. % to about 30 wt. %, in some embodiments from about 0.5 wt. % to about 25 wt. %, and in some embodiments, from about 1 wt. % to about 20 wt. %.

D. Other Components

A wide variety of ingredients may be employed in the composition for a variety of different reasons. For instance, in one particular embodiment, an interphase modifier may be employed in the thermoplastic composition to help reduce the degree of friction and connectivity between the nanoinclusion and/or microinclusion additives and matrix polymer, and thus enhance the degree and uniformity of debonding. In this manner, the pores can become distributed in a more homogeneous fashion throughout the composition. The modifier may be in a liquid or semi-solid form at room temperature (e.g., 25° C.) so that it possesses a relatively low viscosity, allowing it to be more readily incorporated into the thermoplastic composition and to easily migrate to the polymer surfaces. By reducing physical forces at the interfaces of the matrix polymer and the additive, it is believed that the low viscosity, hydrophobic nature of the modifier can help facilitate debonding. As used herein, the term "hydrophobic" typically refers to a material having a contact angle of water in air of about 40° or more, and in some cases, about 60° or more. In contrast, the term "hydrophilic" typically refers to a material having a contact angle of water in air of less than about 40°. One suitable test for measuring the contact angle is ASTM D5725-99 (2008).

Although not required, the interphase modifier may be particularly suitable in embodiments in which a microinclusion additive is employed and in which the nanoinclusion additive is a solid (e.g., polymeric material). Suitable hydrophobic, low viscosity interphase modifiers may include, for instance, the liquids and/or semi-solids referenced above. One particularly suitable interphase modifier is polyether polyol, such as commercially available under the trade name PLURIOL® WI from BASF Corp. Another suitable modifier is a partially renewable ester, such as commercially available under the trade name HALLGREEN® IM from Hallstar.

When employed, the interphase modifier may constitute from about 0.1 wt. % to about 20 wt. %, in some embodiments from about 0.5 wt. % to about 15 wt %, and in some embodiments, from about 1 wt. % to about 10 wt. % of the thermoplastic composition, based on the weight of the continuous phase matrix polymer. The concentration of the interphase modifier in the entire thermoplastic composition may likewise constitute from about 0.05 wt. % to about 20 wt. %, in some embodiments from about 0.1 wt. % to about 15 wt. %, and in some embodiments, from about 0.5 wt. % to about 10 wt. %. In the amounts noted above, the interphase modifier has a character that enables it to readily migrate to the interfacial surface of the polymers and facilitate debonding without disrupting the overall melt properties of the thermoplastic composition. For example, the melt flow rate of the thermoplastic composition may also be similar to that of the matrix polymer. For example, the melt flow rate of the composition (on a dry basis) may be from about 0.1 to about 250 grams per 10 minutes, in some embodiments from about 0.5 to about 200 grams per 10 minutes, and in some embodiments, from about 5 to about 150 grams per 10 minutes, determined at a load of 2160 grams and at 190° C. in accordance with ASTM D1238.

Compatibilizers may also be employed that improve interfacial adhesion and reduce the interfacial tension between the domain and the matrix, thus allowing the formation of smaller domains during mixing. Examples of suitable compatibilizers may include, for instance, copolymers functionalized with epoxy or maleic anhydride chemical moieties. An example of a maleic anhydride compatibilizer is polypropylene-grafted-maleic anhydride, which is commercially available from Arkema under the trade names Orevac™ 18750 and Orevac™ CA 100. When employed, compatibilizers may constitute from about 0.05 wt. % to about 10 wt. %, in some embodiments from about 0.1 wt. % to about 8 wt. %, and in some embodiments, from about 0.5 wt. % to about 5 wt. % of the thermoplastic composition, based on the weight of the continuous phase matrix.

If desired, a butene polymer (homopolymer or copolymer) may also be employed that can act as a plasticizer of the matrix polymer, thereby improving its fluidity and ductility, and in turn, its ability to be processed at relatively high speeds without a substantial degree of breakage. When employed, such butene polymers typically constitute from about 0.01 wt. % to about 15 wt. %, in some embodiments from about 0.1 wt. % to about 12 wt. %, and in some embodiments, from about 0.5 wt. % to about 10 wt. %, based on the weight of the continuous phase (e.g., matrix polymer(s)). The butene polymers may also be employed in an amount of from about 0.01 wt. % to about 15 wt. %, in some embodiments from about 0.1 wt. % to about 12 wt. %, and in some embodiments, from about 0.5 wt. % to about 10 wt. %, based on the total weight of the composition.

The term "butene polymer" generally refers to a homo- or co-polymer of an alkene monomer having four carbon atoms, including 1-butene ($\alpha$-butylene), 2-butene (cis-$\beta$-butylene or trans-$\beta$-butylene), 2-methylpropene (isobutylene), cyclobutene, as well as combinations thereof. The butene polymer may also contain other monomers, such as propene. In one embodiment, for example, the butene polymer may be a homopolymer of butene-1 (referred to as "polybutylene"). Other suitable polymers may include homopolymers of isobutylene (referred to as "polyisobutylene") and copolymers of 1-butene, 2-butene and/or isobutylene (referred to as "polybutene"). In one particular embodiment, for instance, the butene polymer may be polybutylene (also known as poly-1-butene). Polybutylene can be made through a Ziegler-Natta low-pressure polymerization of 1-butene, such as by polymerizing 1-butene with catalysts of $TiCl_3$, $TiCl_3AlCl_3$, and/or $Al(C_2H_5)_2Cl$. While the molecular weight of the butene polymer may vary based on the type of polymer and degree of polymerization, it is typically desired that the butene polymer has a relatively low molecular weight, such as a number average molecular weight of about 10,000 grams per mole or less, in some embodiments about 5,000 grams per mole or less, in some embodiments about 2,000 grams per mole or less, and in some embodiments, from about 100 to about 1,000 grams per mole. Of course, it should be understood that higher molecular weight polymers may also be employed, such as those having a number average molecular weight of from about 10,000 to about 250,000 grams per mole. The density of the butene polymer is also typically about 0.910 grams per cubic centimeter or less, in some embodiments about 0.900 grams per cubic centimeter or less, and in some embodiments, from about 0.810 to about 0.890 grams per cubic centimeter, as determined in accordance with ASTM D4052-11. The kinematic viscosity of the butene polymer may likewise range from about 50 to about 2,000 centistokes ("cs"), in some embodiments from about 100 to about 1,500 cs, and in some embodiments, from about 200 to about 1,000 cs as determined at a temperature of 40° C. in accordance with ASTM D445-14e2.

Other suitable materials that may also be used in the thermoplastic composition, such as catalysts, antioxidants, stabilizers, surfactants, waxes, solid solvents, nucleating agents, particulates, nanofillers, and other materials added to enhance the processability and mechanical properties of the thermoplastic composition. Nevertheless, one beneficial aspect of the present invention is that good properties may be provided without the need for various conventional additives, such as blowing agents (e.g., chlorofluorocarbons, hydrochlorofluorocarbons, hydrocarbons, carbon dioxide, supercritical carbon dioxide, nitrogen, etc.) and pore-initiating fillers (e.g., calcium carbonate). In fact, the thermoplastic composition may be generally free of blowing agents and/or pore-initiating fillers. For example, such blowing agents and/or fillers may be present in an amount of no more than about 1 wt. %, in some embodiments no more than about 0.5 wt. %, and in some embodiments, from about 0.001 wt. % to about 0.2 wt. % of the thermoplastic composition. Further, due to its stress whitening properties, as described in more detail below, the resulting composition may achieve an opaque color (e.g., white) without the need for conventional pigments, such as titanium dioxide. In certain embodiments, for example, pigments may be present in an amount of no more than about 1 wt. %, in some embodiments no more than about 0.5 wt. %, and in some embodiments, from about 0.001 wt. % to about 0.2 wt. % of the thermoplastic composition.

II. Blending

To form the thermoplastic composition, the components are typically blended together using any of a variety of known techniques. In one embodiment, for example, the components may be supplied separately or in combination. For instance, the components may first be dry mixed together to form an essentially homogeneous dry mixture, and they may likewise be supplied either simultaneously or in sequence to a melt processing device that dispersively blends the materials. Batch and/or continuous melt processing techniques may be employed. For example, a mixer/kneader, Banbury mixer, Farrel continuous mixer, single-screw extruder, twin-screw extruder, roll mill, etc., may be utilized to blend and melt process the materials. Particularly suitable melt processing devices may be a co-rotating, twin-screw extruder (e.g., ZSK-30 extruder available from Werner & Pfleiderer Corporation of Ramsey, N.J. or a Thermo Prism™ USALAB 16 extruder available from Thermo Electron Corp., Stone, England). Such extruders may include feeding and venting ports and provide high intensity distributive and dispersive mixing. For example, the components may be fed to the same or different feeding ports of the twin-screw extruder and melt blended to form a substantially homogeneous melted mixture. If desired, other additives may also be injected into the polymer melt and/or separately fed into the extruder at a different point along its length.

Regardless of the particular processing technique chosen, the resulting melt blended composition typically contains nano-scale domains of the nanoinclusion additive and optionally micro-scale domains of the microinclusion additive. The degree of shear/pressure and heat may be controlled to ensure sufficient dispersion, but not so high as to adversely reduce the size of the domains so that they are incapable of achieving the desired properties. For example, blending typically occurs at a temperature of from about 180° C. to about 300° C., in some embodiments from about 185° C. to about 250° C., and in some embodiments, from about 190° C. to about 240° C. Likewise, the apparent shear rate during melt processing may range from about 10 seconds$^{-1}$ to about 3000 seconds$^{-1}$, in some embodiments from about 50 seconds$^{-1}$ to about 2000 seconds$^{-1}$, and in some embodiments, from about 100 seconds$^{-1}$ to about 1200 seconds$^{-1}$. The apparent shear rate may be equal to $4Q/\pi R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, may also be controlled to achieve the desired degree of homogeneity.

To achieve the desired shear conditions (e.g., rate, residence time, shear rate, melt processing temperature, etc.), the speed of the extruder screw(s) may be selected with a certain range. Generally, an increase in product temperature is observed with increasing screw speed due to the additional mechanical energy input into the system. For example, the screw speed may range from about 50 to about 600 revolutions per minute ("rpm"), in some embodiments from about 70 to about 500 rpm, and in some embodiments, from about 100 to about 300 rpm. This may result in a temperature that is sufficiently high to disperse the nanoinclusion additive without adversely impacting the size of the resulting domains. The melt shear rate, and in turn the degree to which the additives are dispersed, may also be increased through the use of one or more distributive and/or dispersive mixing elements within the mixing section of the extruder. Suitable distributive mixers for single screw extruders may include, for instance, Saxon, Dulmage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin (VIP) mixers.

III. Fiber Formation

As used herein, the term "fiber" generally refers to an elongated extrudate formed by passing a polymer through a forming orifice, such as a die. Unless noted otherwise, the term "fiber" includes both discontinuous fibers having a definite length and substantially continuous filaments. Substantially filaments may, for instance, have a length much greater than their diameter, such as a length to diameter ratio ("aspect ratio") greater than about 15,000 to 1, and in some cases, greater than about 50,000 to 1. If desired, the fiber may be "hollow" to such an extent that it contains a hollow cavity extending along at least a portion of the fiber in the longitudinal direction. In some cases, the cavity may extent along the entire length of the fiber.

Fibers formed from the thermoplastic composition may generally have any desired configuration, including monocomponent and multicomponent (e.g., sheath-core configuration, side-by-side configuration, segmented pie configuration, island-in-the-sea configuration, and so forth), shaped fibers (e.g., multi-lobed), etc. Hollow fibers (monocomponent and/or multicomponent) may also be employed, such as described in U.S. Pat. No. 6,642,429 to Carter, et al. In some embodiments, the fibers may contain one or more additional polymers as a component (e.g., bicomponent) or constituent (e.g., biconstituent) to further enhance strength, processibility, and/or other properties. For instance, the thermoplastic composition may form a core component of a sheath/core bicomponent fiber, while an additional polymer may form the sheath component, or vice versa. The additional polymer may be any polymer desired, such as polyesters, e.g., polylactic acid, polyethylene terephthalate, etc.; polyolefins, e.g., polyethylene, polypropylene, polybutylene, and so forth; polytetrafluoroethylene; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; and polyurethanes.

Figure 2:
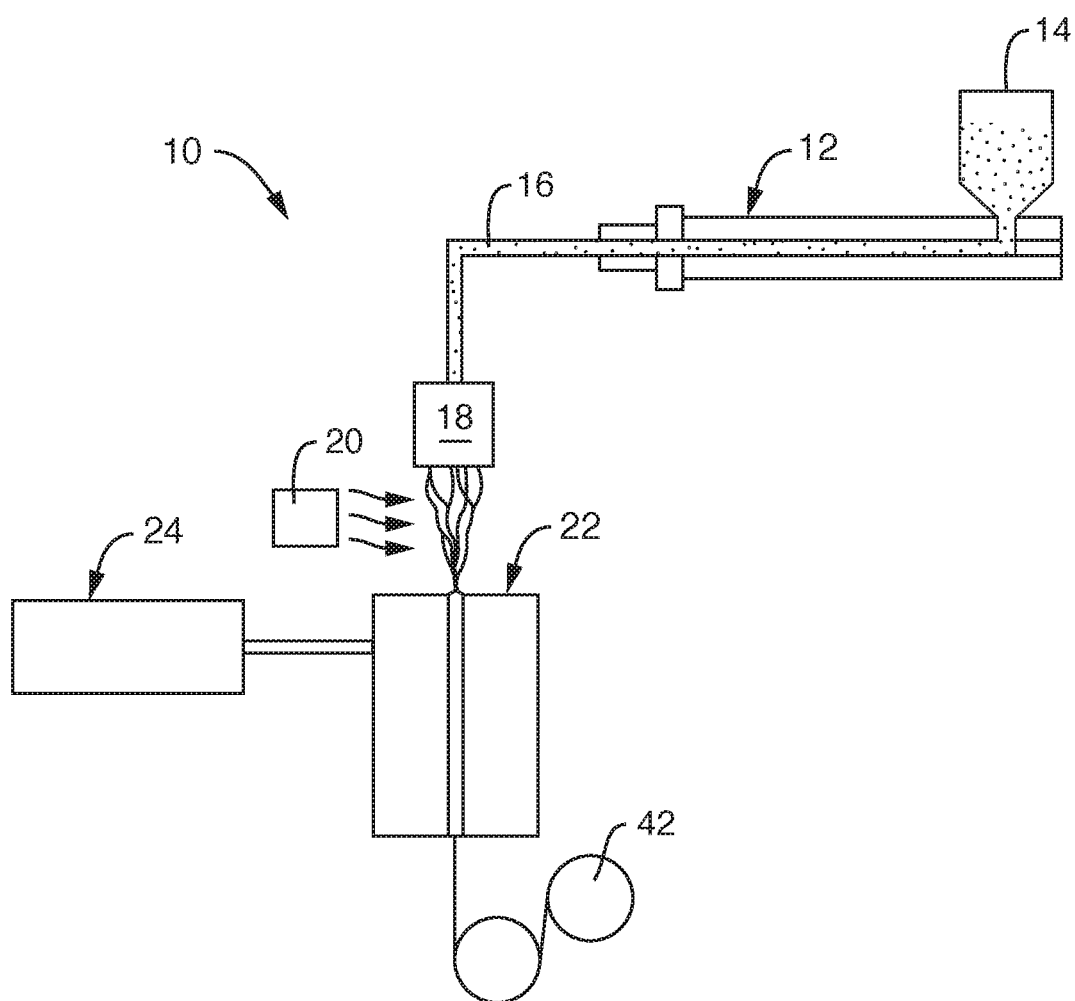
FIG. 2 is a schematic illustration of a process that may be used in one embodiment of the present invention to form fibers.

Regardless of their particular configuration, any of a variety of processes may be used to form the fibers of the present invention. For instance, the fibers may be formed using a process in which the thermoplastic composition is extruded through a die system (or spinneret) that may include a housing containing a spin pack having a plurality of plates stacked one on top of each other and having a pattern of capillaries arranged to create flow paths for directing the thermoplastic composition. Referring to FIG. 2, for example, one embodiment of a method for forming fibers is shown in more detail. In this particular embodiment, the thermoplastic composition of the present invention may be fed into an extruder 12 from a hopper 14. The blend may be provided to the hopper 14 using any conventional technique. The extruder 12 is heated to a temperature sufficient to extrude the melted polymer. The composition is typically melt spun at a temperature of from about 180° C. to about 300° C., in some embodiments from about 200° C. to about 260° C., and in some embodiments, from about 210° C. to about 250° C.

The extruded composition is then passed through a polymer conduit 16 to a spinneret 18 having openings arranged in one or more rows. The openings form a downwardly extruding curtain of filaments when the polymers are extruded therethrough. The process 10 also employs a quench blower 20 positioned adjacent the curtain of fibers extending from the spinneret 18. Air from the quench air blower 20 quenches the fibers extending from the spinneret 18. The quench air may be directed from one side of the fiber curtain as shown in FIG. 2 or both sides of the fiber curtain. To form a fiber with the desired length, the quenched fibers are generally melt drawn, such as using a fiber draw unit 22 as shown in FIG. 2. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255. The fiber draw 22 generally includes an elongated vertical passage through which the fibers are drawn by aspirating air entering from the sides of the passage and flowing downwardly through the passage. A heater or blower 24 supplies aspirating air to the fiber draw unit 22. The aspirating air melt draws the fibers and ambient air through the fiber draw unit 22. The flow of gas causes the fibers to melt draw or attenuate, which increases the molecular orientation or crystallinity of the polymers forming the fibers. When employing a fiber draw unit, the "draw down" ratio may be selected to help achieve the desired fiber length. The "drawn down" ratio is the linear speed of the fibers after drawing (e.g., linear speed of the godet roll 42 or a foraminous surface (not shown) divided by the linear speed of the fibers after extrusion). For example, the draw down ratio during melt drawing may be calculated as follows:

$$\text{Draw Down Ratio} = A/B$$

wherein,

A is the linear speed of the fiber after melt drawing (e.g., godet speed) and is directly measured; and B is the linear speed of the extruded fiber and can be calculated as follows:

$$\text{Extruder linear fiber speed} = C/(25 * \pi * D * E^2)$$

wherein,

C is the throughput through a single hole (grams per minute);

D is the melt density of the polymer (grams per cubic centimeter); and

E is the diameter of the orifice (in centimeters) through which the fiber is extruded. In certain embodiments, the draw down ratio may be from about 5:1 to about 4000:1, in some embodiments from about 10:1 to about 2000:1, and in some embodiments, from about 15:1 to about 1000:1 and in some embodiments from about 20:1 to about 800:1.

Once formed, the fibers may be deposited through the outlet opening of the fiber draw unit 22 and onto a godet roll 42. If desired, the fibers collected on the godet roll 42 may optionally be subjected to additional in line processing and/or converting steps (not shown) as will be understood by those skilled in the art. For example, fibers may be collected and thereafter crimped, texturized, and/or and cut to an average fiber length in the range of from about 3 to about 80 millimeters, in some embodiments from about 4 to about 65 millimeters, and in some embodiments, from about 5 to about 50 millimeters.

A plurality of the resulting fibers may thereafter be provided in a bundle. At least a portion, if not all, of the fibers in the bundle are formed from the thermoplastic composition of the present invention. The bundle typically includes about 5 or more fibers, in some embodiments about 50 or more fibers, in some embodiments from about 100 to about 1000 fibers, and in some embodiments, from about 200 to about 800 fibers. The total fiber denier of the bundle may also range from about 1 to about 30 kilograms per 9000 meters, in some embodiments from about 2 to about 20 kilograms per 9000 meters, and in some embodiments, from about 5 to about 15 kilograms per 9000 meters.

The fibers in the bundle are typically oriented substantially along a longitudinal axis. The fibers may be separated or optionally twisted together about the longitudinal axis. When employed, the nature of the twist may vary as desired. In certain embodiments, for instance, a helical twist (e.g., conical helix, circular helix, etc.) may be employed to form the bundle of fibers. When employed, the angle of the helical twist may vary between about 0.1° to about 20°, in some embodiments from about 0.2° to about 10°, and in some embodiments, from about 0.5° to about 5°. The pitch, which is the linear distance for the bundle to make a complete revolution around the longitudinal axis, may likewise vary from about 1 to about 300 turns per meter, in some embodiments from about 2 to about 200 turns per meter, and in some embodiments, from about 5 to about 100 turns per meter. Any of a variety of different techniques may generally be employed to twist the fibers. In one embodiment, for example, the twist can be created by unwinding fibers from a bobbin over-end as is known in the art. Moreover, other techniques known in the art for twisting multifilament yarns, for example, may also be employed, such as plying, interlacing, etc.

IV. Drawing

As noted above, a bundle of the above-described fibers are drawn by a process that includes traversing the bundle over one or more draw bars. The draw bars may be stationary or rotatable, and can be formed from a wide variety of materials, such as rubbers, metals (e.g., steel), etc. Regardless, the draw bar(s) are in contact with a fluidic medium. Examples of the fluidic medium may include, for instance, water, aqueous solutions containing water and one or more additional solvents (e.g., alcohols), non-aqueous solutions that do not contain water, etc. The initial temperature of the fluidic medium is typically controlled so that it is at least about 10° C., in some embodiments at least about 20° C., and in some embodiments, at least about 30° C. below the melting temperature of the matrix polymer and optionally other components of the composition (e.g., nanoinclusion additive or microinclusion additive). For example, the temperature of the fluidic medium is typically from about −20° C. to about 90° C., in some embodiments from about −10° C. to about 60° C., and in some embodiments, from about 0° C. to about 45° C.

Figure 5:
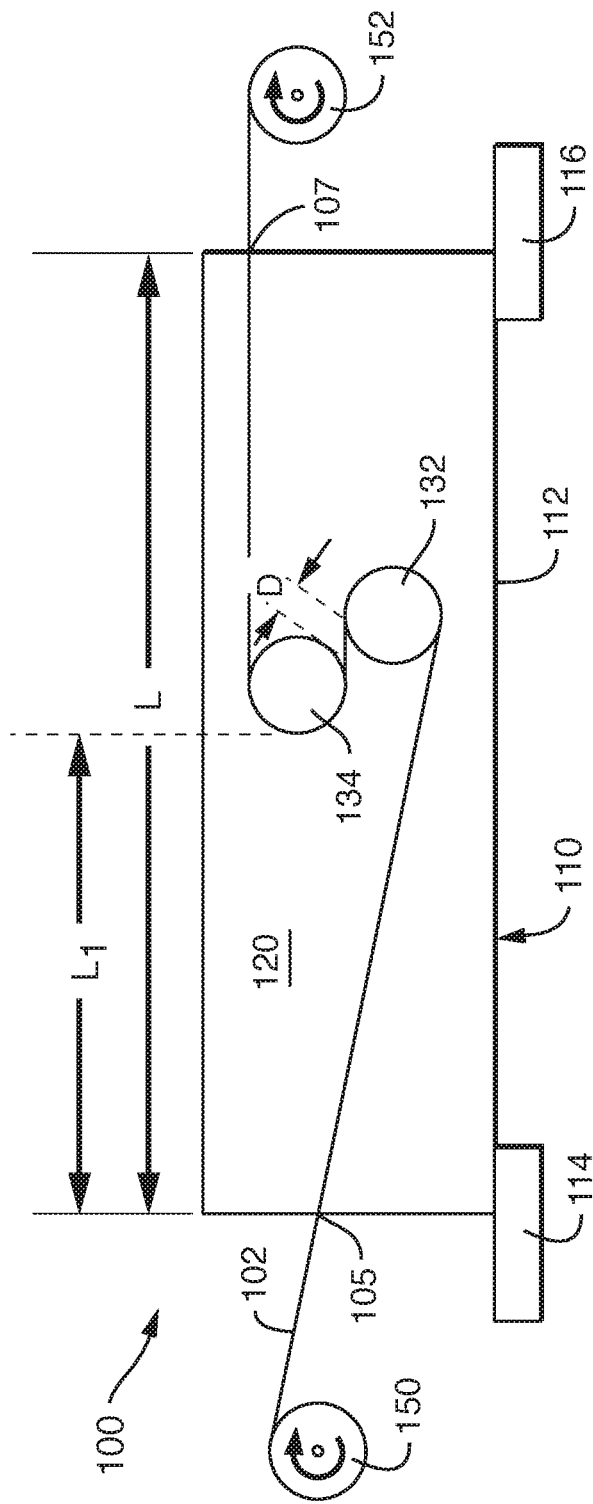
FIG. 5 is a schematic illustration of a system for drawing a bundle of fibers in accordance with one embodiment of the present invention.
Figure 6:
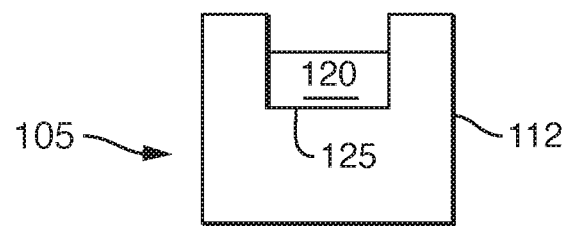
FIG. 6 is a front view of the bath shown in FIG. 5.
Figure 7:
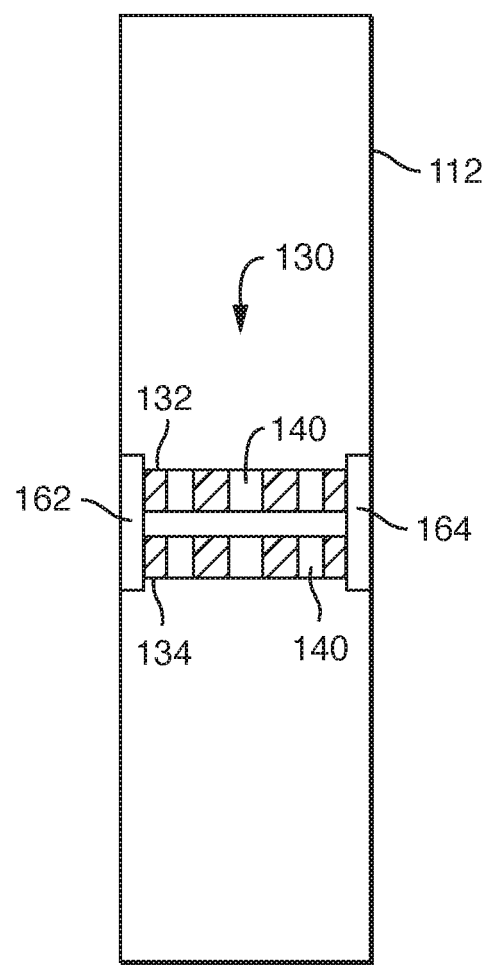
FIG. 7 is a top view of the bath and draw bars shown in FIG. 5.

The specific configuration of the fluidic-based drawing system of the present invention may vary as would be understood by those skilled in the art. Referring to FIGS. 5-7, for instance, one embodiment of a fluidic drawing system 100 is shown in more detail. In this particular configuration, the system 100 includes a bath 110 that contains a chamber 112 within which a fluidic medium 120 (e.g., water) is disposed. First and second draw bars 132 and 134, respectively, are positioned within the bath 110. It should be understood that any number of draw bars may generally be employed in the present invention. In some embodiments, for example, only a single draw bar may be employed. In yet other embodiments, more than two draw bars can even be employed. When multiple bars are employed, the relative spacing between the bars can be selectively controlled to help achieve the desired porous network. As shown in FIG. 5, for instance, the bars 132 and 134 may be spaced apart by a distance "D", which can sometimes vary between about 0.4 to about 50 millimeters, in some embodiments from about 0.5 to about 25 millimeters, and in some embodiments from about 1 to about 10 millimeters. The overall width (e.g., outer diameter) of the bar(s) may also vary, such as from about 1 to about 50 millimeters, in some embodiments from about 2 to about 40 millimeters, and in some embodiments, from about 5 to about 25 millimeters.

If desired, one or more of the draw bars may also be provided with one or more grooves. Referring to FIG. 7, for instance, the draw bars 132 and 134 may each contain multiple grooves 140 that are oriented in a direction generally parallel with the longitudinal direction of the fiber bundle (also known as the "machine direction"). In certain cases, a fiber bundle can pass through a groove to improve cohesion between the fibers, which can help reduce the occurrence of necks and fiber breakage. When employed, the number of grooves 140 contained on a bar typically ranges from 2 and 15 grooves, in some embodiments from t 3 and 12 grooves, and in some embodiments, from 4 to 10 grooves. The grooves 140 may also have a certain depth, which generally ranges from about 0.1 to about 3.0 millimeters, and in some embodiments, from about 0.2 to about 2 millimeters. In addition, the peak-to-peak distance between the grooves 140 is typically from about 0.1 to about 3.0 millimeters, and in some embodiments, from about 0.2 to about 2 millimeters.

If desired, one or more of the draw bar(s) may also be heated to a temperature that is greater than that of the fluidic medium. Such heated draw bar(s) can help control draw by creating a localized soft point in the fiber bundle, thus increasing the probability that fiber deformation/necking will occur at the soft point. For example, the draw bar(s) may be heated to a temperature that is at least about 5° C. greater, in some embodiments at least about 10° C. greater, and in some embodiments, from about 15° C. to about 40° C. greater than the temperature of the fluidic medium. For example, the temperature of the draw bar(s) may be from about 0° C. to about 100° C., in some embodiments from about 10° C. to about 80° C., and in some embodiments, from about 20° C. to about 70° C.

Regardless of the particular configuration employed, the draw bar(s) are positioned so that they are in contact with the fluidic medium 120. Although not necessarily required, it is typically desired that the draw bars 132 and 134 are completely submerged within the fluid medium 120 as shown in FIG. 5. To initiate the drawing process, a fiber bundle 102 may be unwound from a feed roller 150. If desired, multiple feed rollers may also be employed so that the bundle undergoes some degree of drawing prior to entering the fluidic drawing system 100. Regardless, the bundle 102 is supplied to the fluidic drawing system 100 at an entrance 105. As shown in FIG. 6, a slot 125 may be provided in the chamber 112 at the entrance 105. In this manner, the fiber bundle 102 can enter the fluidic medium 120 without having to undergo a substantial change in direction. If desired, the drawing system 100 may also include a tray 114 (FIG. 5) at the entrance 105 to retain any of the fluidic medium 120 that may potentially flow out of the chamber 112 during the drawing operation.

From the entrance, the bundle 102 passes through the fluidic medium 120 until reaching the first draw bar 132. As illustrated, the bundle 102 traverses sequentially over the first draw bar 132 and then the second draw bar 132. The relative orientation of the draw bars 132 and 134 generally dictates the path that the bundle 102 follows as it traverses therethrough. In the illustrated embodiment, for example, the bars 132 and 134 are positioned in an "S-shaped" configuration so that the bundle 102 exits the second bar 134 at an angle that is approximately 180° relative to its position upon entering the first bar 132. Of course, this angle may vary, such as from about 45° to about 250°, in some embodiments from about 60° to about 200°, and in some embodiments, from about 90° to about 180°. In the illustrated embodiment, the bars 132 and 134 are mounted between clamps 162 and 164 (FIG. 7). The use of such clamps can allow the bars to be more readily positioned at the desired angle.

The degree of stretching imparted by the fluidic drawing system of the present invention can be controlled by a variety of factors, including the relative size of the bath through which the bundle traverses. Referring again to FIG. 5, for instance, the length "L" of the chamber 112 may range from about 10 to about 800 centimeters, in some embodiments from about 30 to about 500 centimeters, and in some embodiments, from about 50 to about 300 centimeters. The length "$L_1$" of the chamber through which the fiber 102 is in contact with the fluidic medium 120 prior to first contacting the draw bars is typically a substantial portion of the overall length of the chamber, such as about 60% or more, in some embodiments about 70% or more, and in some embodiments, from about 80% to about 95% of the entire length of the chamber. For instance, the length "$L_1$" may range from about 6 to about 600 centimeters, in some embodiments from about 20 to about 400 centimeters, and in some embodiments, from about 40 to about 200 centimeters.

After traversing over the draw bars 132 and 134, the fiber bundle 102 may exit the chamber 112 at an exit 107 and then wound onto a roller 152 or series of multiple rollers. If desired, the drawing system 100 may also include a tray 116 at the exit 107 to retain any of the fluidic medium 120 that may potentially flow out of the chamber 112. Although not depicted, an air knife may be employed at the exit 107 to help remove water from the fiber bundle 102 as it exits the water bath. To help achieve the desired degree of drawing, the winding roller 152 generally rotates at a velocity that is greater than the velocity at which the feed roller 150 rotates. For example, the ratio of the velocity of the winding roller 152 to the feed roller 150 may be from about 1.1 to about 25, in some embodiments from about 1.5 to about 15, and in some embodiments, from about 2 to about 10. The draw rate may also vary to help achieve the desired properties, such as within the range of from about 5% to about 1500% per minute of deformation, in some embodiments from about 20% to about 1000% per minute of deformation, and in some embodiments, from about 25% to about 850% per minute of deformation.

In the embodiments discussed above, a single drawing stage is employed. It should be understood, however, that this is by no means required. In fact, it may be desirable in certain embodiments of the present invention to employ a multi-stage drawing process that includes at least one fluidic drawing stage, such as described above. Other drawing stages may be in a fluidic medium, or in another medium, such as air. In particularly desirable embodiments, a multi-stage process is employed that contains at least two sequential fluidic drawing stages. Although not necessarily required, the present inventors have discovered that the use of different temperature during sequential fluidic drawing stages can have a beneficial impact on the properties of the resulting fibers. In one embodiment, for instance, the fiber bundle is supplied to a first drawing stage that employs a first fluidic medium having a first temperature. After being drawn during the first stage, the fiber bundle is thereafter supplied to a second drawing stage that employs a second fluidic medium having a second temperature. Both the first and second temperatures are generally lower than the melting temperature of the matrix polymer, as noted above. However, the first temperature may optionally be greater than the second temperature. For instance, the first temperature may be from about 20° C. to about 90° C., and in some embodiments, from about 25° C. to about 60° C., while the second temperature may be from about −10° C. to about 20° C., and in some embodiments, from about 0° C. to about 15° C.

Drawing in the manner described above can result in the formation of a stable porous network without a substantial degree of breakage in the fibers. For example, the average percent volume occupied by the pores within a given unit volume of a fiber may be from about 15% to about 80% per $cm^3$, in some embodiments from about 20% to about 70%, and in some embodiments, from about 30% to about 60% per cubic centimeter of the fiber. With such a pore volume, the fiber (e.g. polyolefin fiber) may have a relatively low density, such as about 1.1 grams per cubic centimeter ("$g/cm^3$") or less, in some embodiments about 0.90 $g/cm^3$ or less, in some embodiments about 0.85 $g/cm^3$ or less, in some embodiments about 0.80 $g/cm^3$ or less, in some embodiments from about 0.10 $g/cm^3$ to about 0.75 $g/cm^3$, and in some embodiments, from about 0.20 $g/cm^3$ to about 0.70 $g/cm^3$. A substantial portion of pores in the porous network are also of a "nano-scale" size ("nanopores"), such as those having an average cross-sectional dimension of about 800 nanometers or less, in some embodiments from about 5 to about 700 nanometers, and in some embodiments, from about 10 to about 500 nanometers. The term "cross-sectional dimension" generally refers to a characteristic dimension (e.g., width or diameter) of a pore, which is substantially orthogonal to its major axis (e.g., length) and also typically substantially orthogonal to the direction of the stress applied during drawing. The nanopores may also have an average axial dimension within the range of from about 100 to about 5000 nanometers, in some embodiments from about 50 to about 2000 nanometers, and in some embodiments, from about 100 to about 1000 nanometers. The "axial dimension" is the dimension in the direction of the major axis (e.g., length), which is typically in the direction of drawing. Such nanopores may, for example, constitute about 15 vol. % or more, in some embodiments about 20 vol. % or more, in some embodiments from about 30 vol. % to 100 vol. %, and in some embodiments, from about 40 vol. % to about 90 vol. % of the total pore volume in a fiber.

Micropores may also be formed during drawing that have an average cross-sectional dimension of about 0.2 micrometers or more, in some embodiments about 0.5 micrometers or more, and in some embodiments, from about 0.5 micrometers to about 5 micrometers. In certain cases, the axial dimension of the micropores and/or nanopores may be larger than the cross-sectional dimension so that the aspect ratio (the ratio of the axial dimension to the cross-sectional dimension) is from about 1 to about 30, in some embodiments from about 1.1 to about 15, and in some embodiments, from about 1.2 to about 5. For example, the axial dimension of the micropores may be 1 micrometer or more, in some embodiments about 1.5 micrometers or more, and in some embodiments, from about 2 to about 30 micrometers.

Regardless of their particular size, the present inventors have discovered that the pores (e.g., nanopores, micropores, or both) can be distributed in a substantially homogeneous fashion throughout the composition. For example, the pores may be distributed in columns that are oriented in a direction generally perpendicular to the direction in which a stress is applied. These columns may be generally parallel to each other across the width of the composition. Without intending to be limited by theory, it is believed that the presence of such a homogeneously distributed porous network can result in good mechanical properties (e.g., energy dissipation under load and impact strength). This is in stark contrast to conventional techniques for creating pores that involve the use of blowing agents, which tend to result in an uncontrolled pore distribution and poor mechanical properties.

In addition to forming a porous network, drawing can also significantly increase the axial dimension of certain of the discrete domains so that they have a generally linear, elongated shape. For example, the elongated micro-scale domains may have an axial dimension that is about 10% or more, in some embodiments from about 20% to about 500%, and in some embodiments, from about 50% to about 250% greater than the axial dimension of the domains prior to drawing. The axial dimension (e.g., length) after drawing may, for instance, range from about 1 μm to about 400 μm, in some embodiments from about 5 μm to about 200 μm, and in some embodiments from about 10 µm to about 150 µm. The micro-scale domains may also be relatively thin and thus have a small cross-sectional dimension, such as from about 0.02 to about 20 micrometers, in some embodiments from about 0.1 to about 10 micrometers, and in some embodiments, from 0.4 to about 5 micrometers. This may result in an aspect ratio for the domains (the ratio of the axial dimension to a dimension orthogonal to the axial dimension) of from about 2 to about 150, in some embodiments from about 3 to about 100, and in some embodiments, from about 4 to about 50. Due to their small size, the nano-scale domains are not typically elongated in the same manner as the micro-scale domains. Thus, the nano-scale domains may retain an average axial dimension (e.g., length) of from about 1 to about 1000 nanometers, in some embodiments from about 5 to about 800 nanometers, in some embodiments from about 10 to about 500 nanometers, and in some embodiments from about 20 to about 200 nanometers.

Even at the very low densities achieved by the present invention, the resulting fibers are not brittle and thus can deform upon the application of strain, rather than fracture. The fibers may thus continue to function as a load bearing member even after the fiber has exhibited substantial elongation. In this regard, the fibers of the present invention are capable of exhibiting improved "peak elongation properties, i.e., the percent elongation of the fiber at its peak load. For example, the fibers of the present invention may exhibit a peak elongation of about 50% or more, in some embodiments about 100% or more, in some embodiments from about 200% to about 1500%, and in some embodiments, from about 400% to about 800%, such as determined in accordance with ASTM D638-10 at 23° C. Such elongations may be achieved for fibers having a wide variety of average diameters, such as those ranging from about 0.1 to about 50 micrometers, in some embodiments from about 1 to about 40 micrometers, in some embodiments from about 2 to about 25 micrometers, and in some embodiments, from about 5 to about 15 micrometers.

While possessing the ability to extend under strain, the fibers of the present invention can also remain relatively strong. For example, the fibers may exhibit a peak tensile stress of from about 25 to about 600 Megapascals ("MPa"), in some embodiments from about 50 to about 450 MPa, and in some embodiments, from about 60 to about 350 MPa, such as determined in accordance with ASTM D638-10 at 23° C. Another parameter that is indicative of the relative strength of the fibers of the present invention is "tenacity", which indicates the tensile strength of a fiber expressed as force per unit linear density. For example, the fibers of the present invention may have a tenacity of from about 0.75 to about 7.0 grams-force ("$g_f$") per denier, in some embodiments from about 1.0 to about 6.0 $g_f$ per denier, and in some embodiments from about 1.5 to about 5.0 $g_f$ per denier. The denier of the fibers may vary depending on the desired application. Typically, the fibers are formed to have a denier per filament (i.e., the unit of linear density equal to the mass in grams per 9000 meters of fiber) of less than about 15, in some embodiments less than about 12, and in some embodiments, from about 0.5 to about 6.

V. Fibrous Material

After drawing, the fiber bundle may be separated so that the individual fibers can be employed in various applications. Alternatively, the fiber bundle itself may be employed in the desired application. The fibers and/or fiber bundle may be employed alone or further processed into a fibrous material, such as a woven fabric, knit fabric, nonwoven web, etc. For example, individual fibers derived from the drawn fiber bundle can be formed into a coherent nonwoven web structure by randomly depositing the fibers onto a forming surface (optionally with the aid of a vacuum) and then bonding the resulting web using any known technique.

The nonwoven web may be bonded using any conventional technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with the polymer used to form the fibers. Suitable autogenous bonding techniques may include ultrasonic bonding, thermal bonding, through-air bonding, calendar bonding, and so forth. For example, the web may be further bonded or embossed with a pattern by a thermo-mechanical process in which the web is passed between a heated smooth anvil roll and a heated pattern roll. The pattern roll may have any raised pattern which provides the desired web properties or appearance. Desirably, the pattern roll defines a raised pattern which defines a plurality of bond locations which define a bond area between about 2% and 30% of the total area of the roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., as well as U.S. Design Pat. Nos. 428,267 to Romano et al.; 390,708 to Brown; 418,305 to Zander, et al.; 384,508 to Zander, et al.; 384,819 to Zander, et al.; 358,035 to Zander, et al.; and 315,990 to Blenke, et al. The pressure between the rolls may be from about 5 to about 2000 pounds per lineal inch. The pressure between the rolls and the temperature of the rolls is balanced to obtain desired web properties or appearance while maintaining cloth like properties. As is well known to those skilled in the art, the temperature and pressure required may vary depending upon many factors including but not limited to, pattern bond area, polymer properties, fiber properties and nonwoven properties.

In addition to spunbond webs, a variety of other nonwoven webs may also be formed from the thermoplastic composition in accordance with the present invention, such as meltblown webs, bonded carded webs, wet-laid webs, airlaid webs, coform webs, hydraulically entangled webs, etc. For example, the thermoplastic composition may be extruded through a plurality of fine die capillaries into a converging high velocity gas (e.g., air) streams that attenuate the fibers to reduce their diameter. Thereafter, the meltblown fibers are carried by the high velocity gas stream and are deposited on a collecting surface to form a web of randomly dispersed meltblown fibers. Alternatively, the polymer may be formed into a carded web by placing bales of fibers formed from the thermoplastic composition into a picker that separates the fibers. Next, the fibers are sent through a combing or carding unit that further breaks apart and aligns the fibers in the machine direction so as to form a machine direction-oriented fibrous nonwoven web. Once formed, the nonwoven web is typically stabilized by one or more known bonding techniques as described above to form a bonded carded web.

If desired, the nonwoven web may also be a composite that contains a combination of the fibers of the present invention and other types of fibers (e.g., staple fibers, filaments, etc.). For example, additional synthetic fibers may be utilized, such as those formed from polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; etc. If desired, renewable polymers may also be employed. Some examples of known synthetic fibers include sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del. Polylactic acid staple fibers may also be employed, such as those commercially available from Far Eastern Textile, Ltd. of Taiwan.

The composite may also contain pulp fibers, such as high-average fiber length pulp, low-average fiber length pulp, or mixtures thereof. One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas fir, true firs, pine (e.g., southern pines), spruce (e.g., black spruce), bamboo, combinations thereof, and so forth. Northern softwood kraft pulp fibers may be used in the present invention. An example of commercially available southern softwood kraft pulp fibers suitable for use in the present invention include those available from Weyerhaeuser Company with offices in Federal Way, Washington under the trade designation of "NF-405." Another suitable pulp for use in the present invention is a bleached, sulfate wood pulp containing primarily softwood fibers that is available from Bowater Corp. with offices in Greenville, S.C. under the trade name CoosAbsorb S pulp. Low-average length fibers may also be used in the present invention. An example of suitable low-average length pulp fibers is hardwood kraft pulp fibers. Hardwood kraft pulp fibers are derived from deciduous trees and include pulp fibers such as, but not limited to, *eucalyptus*, maple, birch, aspen, etc. *Eucalyptus* kraft pulp fibers may be particularly desired to increase softness, enhance brightness, increase opacity, and change the pore structure of the sheet to increase its wicking ability. Bamboo or cotton fibers may also be employed.

Nonwoven composites may be formed using a variety of known techniques. For example, the nonwoven composite may be a "coform material" that contains a mixture or stabilized matrix of the thermoplastic composition fibers and an absorbent material. As an example, coform materials may be made by a process in which at least one meltblown die head is arranged near a chute through which the absorbent materials are added to the web while it is forming. Such absorbent materials may include, but are not limited to, pulp fibers, superabsorbent particles, inorganic and/or organic absorbent materials, treated polymeric staple fibers, and so forth. The relative percentages of the absorbent material may vary over a wide range depending on the desired characteristics of the nonwoven composite. For example, the nonwoven composite may contain from about 1 wt. % to about 60 wt. %, in some embodiments from 5 wt. % to about 50 wt. %, and in some embodiments, from about 10 wt. % to about 40 wt. % thermoplastic composition fibers. The nonwoven composite may likewise contain from about 40 wt. % to about 99 wt. %, in some embodiments from 50 wt. % to about 95 wt. %, and in some embodiments, from about 60 wt. % to about 90 wt. % absorbent material. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.

Nonwoven laminates may also be formed in the present invention in which one or more layers are formed from the thermoplastic composition. For example, the nonwoven web of one layer may be a spunbond that contains the thermoplastic composition, while the nonwoven web of another layer contains thermoplastic composition, other renewable polymer(s), and/or any other polymer (e.g., polyolefins). In one embodiment, the nonwoven laminate contains a meltblown layer positioned between two spunbond layers to form a spunbond/meltblown/spunbond ("SMS") laminate. If desired, the spunbond layer(s) may be formed from the thermoplastic composition. The meltblown layer may be formed from the thermoplastic composition, other renewable polymer(s), and/or any other polymer (e.g., polyolefins). Various techniques for forming SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., as well as U.S. Patent Application Publication No. 2004/0002273 to Fitting, et al. Of course, the nonwoven laminate may have other configuration and possess any desired number of meltblown and spunbond layers, such as spunbond/meltblown/meltblown/spunbond laminates ("SMMS"), spunbond/meltblown laminates ("SM"), etc. Although the basis weight of the nonwoven laminate may be tailored to the desired application, it generally ranges from about 10 to about 300 grams per square meter ("gsm"), in some embodiments from about 25 to about 200 gsm, and in some embodiments, from about 40 to about 150 gsm.

Nonwoven-film laminates may also be formed. In such embodiments, the film is typically liquid-impermeable and either vapor-permeable or vapor-impermeable. Films that are liquid-impermeable and vapor-permeable are often referred to as "breathable" and they typically have a water vapor transmission rate ("WVTR") of about 100 grams per square meter per 24 hours ($g/m^2/24$ hours) or more, in some embodiments from about 500 to about 20,000 $g/m^2/24$ hours, and in some embodiments, from about 1,000 to about 15,000 $g/m^2/24$ hours. The breathable film may also be a microporous or monolithic film. Microporous films are typically formed by incorporating a filler (e.g., calcium carbonate) into the polymer matrix, and thereafter stretching the film to create the pores. Examples of such films are described, for instance, in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack, et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al.

If desired, the fibers, nonwoven web, etc., may also be annealed to help ensure that they retains the desired shape. Annealing typically occurs at temperatures of from about 40° C. to about 120° C., in some embodiments from about 50° C. to about 110° C., and in some embodiments, from about 80° C. to about 100° C. The fibers may also be surface treated using any of a variety of known techniques to improve its properties. For example, high energy beams (e.g., plasma, x-rays, e-beam, etc.) may be used to remove or reduce any skin layers that form on the fibers, to change the surface polarity, embrittle a surface layer, etc. If desired, such surface treatment may be used before and/or after formation of a web, as well as before and/or after cold drawing of the fibers.

VI. Articles

The fibers of the present invention may be employed in a wide variety of different articles. In one embodiment, for instance, the fibers may be employed in an absorbent article. An absorbent article that is capable of absorbing water or other fluids. Examples of some absorbent articles include, but are not limited to, personal care absorbent articles, such as diapers, training pants, absorbent underpants, adult incontinence articles, feminine hygiene products (e.g., sanitary napkins), swim wear, baby wipes, mitt wipes, and so forth; medical absorbent articles, such as garments, fenestration materials, underpads, bandages, absorbent drapes, and medical wipes; food service wipers; clothing articles; and so forth. Regardless of the intended application, the absorbent article typically contains an absorbent member (e.g., core layer, surge layer, transfer delay layer, wrapsheet, ventilation layer, etc.) positioned between a backsheet and a topsheet. Notably, the absorbent member, backsheet, and/or topsheet, as well one or more other components of the absorbent article (e.g., ears, containment flaps, side panels, waist or leg bands, etc.) may include the fibers of the present invention, either alone or in the form of a nonwoven web containing such fibers.

In this regard, various exemplary embodiments of the absorbent article will be described. Referring to FIG. 1, for instance, one particular embodiment of an absorbent article 201 is shown in the form of a diaper. However, as noted above, the invention may be embodied in other types of absorbent articles, such as incontinence articles, sanitary napkins, diaper pants, feminine napkins, training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, and absorbent member that includes an absorbent core layer 203 and surge layer 207. It should be understood, however, that other layers may also be used in the present invention. Likewise, one or more of the layers referred to in FIG. 1 may also be eliminated in certain embodiments of the present invention.

As indicated above, the backsheet 217 may contain the fibers of the present invention, optionally in the form of a nonwoven web. For example, the nonwoven web may be positioned so that it defines a garment-facing surface 333 of the absorbent article 201. The absorbent article 201 also includes a topsheet 205. The topsheet 205 is generally designed to contact the body of the user and is liquid-permeable. For example, the topsheet 205 may define a body-facing surface 218, which is typically compliant, soft feeling, and non-irritating to the wearers skin. If desired, the topsheet 205 may contain the fibers of the present invention, optionally in the form of a nonwoven web. For example, a nonwoven web may be positioned so that it defines the body-facing surface 218 if so desired. The topsheet may surround the absorbent core layer 203 so that it completely encases the absorbent article. Alternatively, the topsheet 205 and the backsheet 217 may extend beyond the absorbent member and be peripherally joined together, either entirely or partially, using known techniques, such as by adhesive bonding, ultrasonic bonding, etc. As indicated above, the topsheet 205 may include a nonwoven web formed according to the present invention. The topsheet 205 may also include a conventional a nonwoven web (e.g., spunbond web, meltblown web, or bonded carded web). Other exemplary topsheet constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941. The topsheet 205 may also contain a plurality of apertures formed therethrough to permit body fluid to pass more readily into the absorbent core layer 203. The apertures may be randomly or uniformly arranged throughout the topsheet 205, or they may be located only in the narrow longitudinal band or strip arranged along the longitudinal axis of the absorbent article. The apertures permit rapid penetration of body fluid down into the absorbent member. The size, shape, diameter and number of apertures may be varied to suit one's particular needs.

The absorbent article also contains an absorbent member positioned between the topsheet and the backsheet. The absorbent member may be formed from a single absorbent layer or a composite containing separate and distinct absorbent layer. It should be understood, however, that any number of absorbent layers may be utilized in the present invention. In FIG. 1, for instance, the absorbent member contains an absorbent core layer 203 and a surge layer 207 that helps to decelerate and diffuse surges or gushes of liquid that may be rapidly introduced into the absorbent core layer 203. Desirably, the surge layer 207 rapidly accepts and temporarily holds the liquid prior to releasing it into the storage or retention portions of the absorbent core layer 203. In the illustrated embodiment, for example, the surge layer 207 is interposed between an inwardly facing surface 216 of the topsheet 205 and the absorbent core layer 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. In one embodiment, the surge layer 207 may contain the fibers of the present invention, optionally in the form of a nonwoven web. Other examples of suitable surge layers are described in U.S. Pat. No. 5,486,166 to Ellis, et al. and U.S. Pat. No. 5,490,846 to Ellis, et al.

If desired, the absorbent member may also contain a transfer delay layer positioned vertically below the surge layer. The transfer delay layer may contain a material that is less hydrophilic than the other absorbent layers, and may generally be characterized as being substantially hydrophobic. For example, the transfer delay layer may be a nonwoven web (e.g., spunbond web) formed from the fibers of the present invention. The fibers may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. To adjust the performance of the invention, the transfer delay layer may also be treated with a selected amount of surfactant to increase its initial wettability.

The transfer delay layer may generally have any size, such as a length of about 150 mm to about 300 mm. Typically, the length of the transfer delay layer is approximately equal to the length of the absorbent article. The transfer delay layer may also be equal in width to the surge layer, but is typically wider. For example, the width of the transfer delay layer may be from between about 50 mm to about 75 mm, and particularly about 48 mm. The transfer delay layer typically has a basis weight less than that of the other absorbent members. For example, the basis weight of the transfer delay layer is typically less than about 150 grams per square meter (gsm), and in some embodiments, between about 10 gsm to about 100 gsm. If desired, the transfer delay layer may contain the fibers of the present invention, optionally in the form of a nonwoven web.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core layer 203. The wrapsheet is typically placed about the absorbent core layer 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core layer 203. The wrapsheet material on one side of the absorbent fibrous mass may be bonded to the wrapsheet located on the opposite side of the fibrous mass to effectively entrap the absorbent core layer 203. Furthermore, the absorbent article 201 may also include a ventilation layer (not shown) that is positioned between the absorbent core layer 203 and the backsheet 217. When utilized, the ventilation layer may help insulate the backsheet 217 from the absorbent core layer 203, thereby reducing dampness in the backsheet 217. Examples of such ventilation layers may include a nonwoven web laminated to a breathable film, such as described in U.S. Pat. No. 6,663,611 to Blaney, et al. If desired, the wrapsheet and/or ventilation layer may contain the fibers of the present invention, optionally in the form of a nonwoven web.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface, which may include the fibers of the present invention, optionally in the form of a nonwoven web. In alternative configurations, the ears may be provided by members connected and assembled to the backsheet 217, the top surface, between the backsheet 217 and top surface, or in various other configurations. As noted above, the ears may contain the fibers of the present invention, optionally in the form of a nonwoven web.

As representatively illustrated in FIG. 1, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core layer 203. The containment flaps 212 may extend longitudinally along the entire length of the absorbent core layer 203, or may only extend partially along the length of the absorbent core layer 203. When the containment flaps 212 are shorter in length than the absorbent core layer 203, they may be selectively positioned anywhere along the side edges 232 of absorbent article 201 in a crotch region 210. In one embodiment, the containment flaps 212 extend along the entire length of the absorbent core layer 203 to better contain the body exudates. Such containment flaps 212 are generally well known to those skilled in the art. For example, suitable constructions and arrangements for the containment flaps 212 are described in U.S. Pat. No. 4,704,116 to Enloe. If desired, the containment flaps may contain the fibers of the present invention, optionally in the form of a nonwoven web.

The absorbent article 201 may include various elastic or stretchable materials, such as a pair of leg elastic members 206 affixed to the side edges 232 to further prevent leakage of body exudates and to support the absorbent core layer 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 1 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing. The elastic members (e.g., leg, waist, etc.) and/or fasteners may contain the fibers of the present invention if desired, optionally in the form of a nonwoven web.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core layer 203 using an adhesive. Alternatively, the absorbent core layer 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth.

The present invention may be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes, typically at 190° C., 210° C., or 230° C. Unless otherwise indicated, melt flow rate is measured in accordance with ASTM Test Method D1238-13 with a Tinius Olsen Extrusion Plastometer.

Thermal Properties:

The glass transition temperature ($T_g$) may be determined by dynamic mechanical analysis (DMA) in accordance with ASTM E1640-09. A Q800 instrument from TA Instruments may be used. The experimental runs may be executed in tension/tension geometry, in a temperature sweep mode in the range from −120° C. to 150° C. with a heating rate of 3° C./min. The strain amplitude frequency may be kept constant (2 Hz) during the test. Three (3) independent samples may be tested to get an average glass transition temperature, which is defined by the peak value of the tan δ curve, wherein tan δ is defined as the ratio of the loss modulus to the storage modulus (tan δ=E"/E').

The melting temperature may be determined by differential scanning calorimetry (DSC). The differential scanning calorimeter may be a DSC Q100 Differential Scanning calorimeter, which was outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools are used. The samples are placed into an aluminum pan and weighed to an accuracy of 0.01 milligram on an analytical balance. A lid is crimped over the material sample onto the pan. Typically, the resin pellets are placed directly in the weighing pan.

The differential scanning calorimeter is calibrated using an indium metal standard and a baseline correction is performed, as described in the operating manual for the differential scanning calorimeter. A material sample is placed into the test chamber of the differential scanning calorimeter for testing, and an empty pan is used as a reference. All testing is run with a 55-cubic centimeter per minute nitrogen (industrial grade) purge on the test chamber. For resin pellet samples, the heating and cooling program is a 2-cycle test that began with an equilibration of the chamber to −30° C., followed by a first heating period at a heating rate of 10° C. per minute to a temperature of 200° C., followed by equilibration of the sample at 200° C. for 3 minutes, followed by a first cooling period at a cooling rate of 10° C. per minute to a temperature of −30° C., followed by equilibration of the sample at −30° C. for 3 minutes, and then a second heating period at a heating rate of 10° C. per minute to a temperature of 200° C. All testing is run with a 55-cubic centimeter per minute nitrogen (industrial grade) purge on the test chamber.

The results are evaluated using the UNIVERSAL ANALYSIS 2000 analysis software program, which identified and quantified the glass transition temperature ($T_g$) of inflection, the endothermic and exothermic peaks, and the areas under the peaks on the DSC plots. The glass transition temperature is identified as the region on the plot-line where a distinct change in slope occurred, and the melting temperature is determined using an automatic inflection calculation.

Tensile Properties:

The tensile properties may be determined in accordance with ASTM 638-10 at 23° C. For instance, individual fiber specimens may initially be shortened (e.g., cut with scissors) to 38 millimeters in length, and placed separately on a black velvet cloth. 10 to 15 fiber specimens may be collected in this manner. The fiber specimens may then be mounted in a substantially straight condition on a rectangular paper frame having external dimension of 51 millimeters×51 millimeters and internal dimension of 25 millimeters×25 millimeters. The ends of each fiber specimen may be operatively attached to the frame by carefully securing the fiber ends to the sides of the frame with adhesive tape. Each fiber specimen may be measured for its external, relatively shorter, cross-fiber dimension employing a conventional laboratory microscope, which may be properly calibrated and set at 40× magnification. This cross-fiber dimension may be recorded as the diameter of the individual fiber specimen. The frame helps to mount the ends of the sample fiber specimens in the upper and lower grips of a constant rate of extension type tensile tester in a manner that avoids excessive damage to the fiber specimens.

A constant rate of extension type of tensile tester and an appropriate load cell may be employed for the testing. The load cell may be chosen (e.g., 10N) so that the test value falls within 10-90% of the full scale load. The tensile tester (i.e., MTS SYNERGY 200) and load cell may be obtained from MTS Systems Corporation of Eden Prairie, Mich. The fiber specimens in the frame assembly may then be mounted between the grips of the tensile tester such that the ends of the fibers may be operatively held by the grips of the tensile tester. Then, the sides of the paper frame that extend parallel to the fiber length may be cut or otherwise separated so that the tensile tester applies the test force only to the fibers. The fibers may be subjected to a pull test at a pull rate and grip speed of 12 inches per minute. The resulting data may be analyzed using a TESTWORKS 4 software program from the MTS Corporation with the following test settings:

| Calculation Inputs | | Test Inputs | |
|---|---|---|---|
| Break mark drop | 50% | Break sensitivity | 90% |
| Break marker elongation | 0.1 in | Break threshold | 10 $g_f$ |
| Nominal gage length | 1 in | Data Acq. Rate | 10 Hz |
| Slack pre-load | 1 $lb_f$ | Denier length | 9000 m |
| Slope segment length | 20% | Density | 1.25 g/cm$^3$ |
| Yield offset | 0.20% | Initial speed | 12 in/min |
| Yield segment length | 2% | Secondary speed | 2 in/min |

The tenacity values may be expressed in terms of gram-force per denier. Peak elongation (% strain at break) and peak stress may also be measured.

The peak load of a web may be determined using a 2"×6" strip cut along the length (MD) and width direction (CD). The test may be performed in a universal tensile tester equipped with two 1"×3" rubber coated grips. The gauge length may be 76±1 mm (3±0.04").

Percent Void Volume:

To percent void volume, the width ($W_i$) and thickness ($T_i$) of the specimen may be initially measured prior to drawing. The length ($L_i$) before drawing may also be determined by measuring the distance between two markings on a surface of the specimen. Thereafter, the specimen may be drawn to initiate pore formation. The width ($W_f$), thickness ($T_f$), and length ($L_f$) of the specimen may then be measured to the nearest 0.01 mm utilizing Digimatic Caliper (Mitutoyo Corporation). The volume ($V_i$) before drawing may be calculated by $W_i \times T_i \times L_i = V_i$. The volume ($V_f$) after drawing may also be calculated by $W_f \times T_f \times L_f = V_f$.

Fiber Density:

To measure density, the fibers where placed in solutions of known densities at ambient conditions. If the fibers floated in a given solution, the density was determined to be less than given solution. If the fibers sank in a given solution, the density was greater than the given solution. The table below summarizes the solution used during testing, wherein the density of each solution was determined using hydrometers.

| Solution | Density (g/cc) |
|---|---|
| 100 vol. % Hexanes | 0.66 |
| 25 vol. % 2-propanol/75% Hexanes | 0.69 |
| 50 vol. % 2-propanol/50% Hexanes | 0.72 |
| 75 vol. % 2-propanol/25% Hexanes | 0.75 |
| 100 vol. % 2-propanol | 0.78 |
| 85% 2-propanol 15% water | 0.83 |
| 70% 2-propanol 30% water | 0.87 |

Hydrostatic Pressure Test ("Hydrohead"):

The hydrostatic pressure test is a measure of the resistance of a material to penetration by liquid water under a static pressure and is performed in accordance with AATCC Test Method 127-2008. The results for each specimen may be averaged and recorded in centimeters (cm). A higher value indicates greater resistance to water penetration.

Water Vapor Transmission Rate ("WVTR"):

The test used to determine the WVTR of a material may vary based on the nature of the material. One technique for measuring the WVTR value is ASTM E96/96M-12, Procedure B. Another method involves the use of INDA Test Procedure IST-70.4 (01). The INDA test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modem Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow that is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material,guardfilm,airgap} - TR^{-1}_{guardfilm,airgap}$$

The water vapor transmission rate ("WVTR") is then calculated as follows:

$$WVTR = \frac{F \rho_{sat(T)} RH}{A P_{sat(T)} (1 - RH)}$$

wherein,

F=the flow of water vapor in $cm^3$ per minute;

$\rho_{sat}(T)$=the density of water in saturated air at temperature T;

RH=the relative humidity at specified locations in the cell;

A=the cross sectional area of the cell; and $P_{sat}(T)$=the saturation vapor pressure of water vapor at temperature T.

Frazier Porosity:

The Frazier porosity was measured in a Frazier® Low Differential Pressure Air Permeability Tester (FAP-LP) by cutting an 8" strip (measured along the machine direction) of a sample and folding the sample accordion style (in the cross direction) to obtain six layers.

Example 1

Figure 3:
FIGS. 3-4 are SEM microphotographs of the fibers of Example 1.
Figure 4:
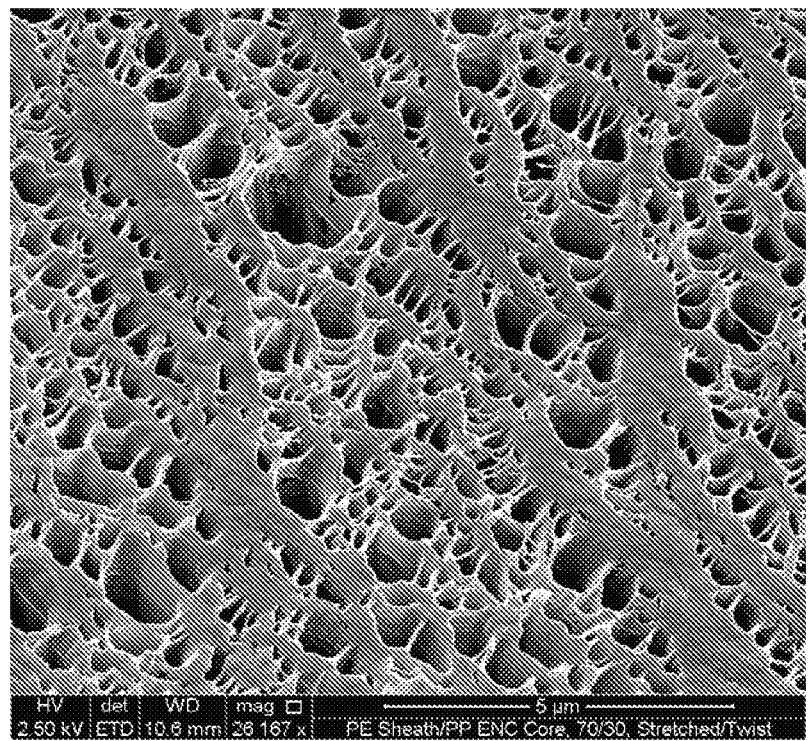

Bicomponent fibers were formed that contained a core formed from a blend of 93 wt. % isotactic polypropylene (M3661, melt flow rate of 14 g/10 min at 230° C. and melting temperature of 150° C., Total Petrochemicals) and 7 wt. % LOTADER® AX8900 (Arkema), and a sheath formed from 100 wt. % ASPUN™ 6835A (LLDPE, from Dow Chemical). The core was 70 vol. % of the fiber and the sheath was 30 vol. %. A bundle was formed that contained 288 of the fibers. The total bundle denier was approximately 11 kilograms per 9000 meters. A bobbin containing the precursor bundle of fibers was unwound over-end to provide a slight twist to the bundle of approximately 1 to 2 turns per meter. The bundle was taken-up using a set of 5 rollers (quintet) at a speed of 14 meters per minute. The bundle was then immersed in a water bath (40° C.) where it was drawn with two draw bars positioned perpendicular to the direction of fiber travel. Each draw bar had a diameter of 12.5 mm. The draw bars were set parallel with each other and spaced apart by a gap of 8 mm. As shown in FIG. 5, this configuration caused the bundle to follow a 180-degree turn (s-wrap) before exiting the water bath. After emerging from the water bath, the bundle was taken up by two quintets, which both ran at a speed of 84 meters per minute to give a total draw ratio if 6. SEM microphotographs of the resulting bundle are shown in FIGS. 3-4.

Example 2

Bicomponent fibers were formed that contained a core formed from a blend of 93 wt. % isotactic polypropylene (M3661 Total Petrochemicals) and 7 wt. % LOTADER® AX8900 (Arkema), and a sheath formed from 100 wt. % ASPUN™ 6835A (LLDPE, from Dow Chemical). The core was 70 vol. % of the fiber and the sheath was 30 vol. %. A bundle was formed that contained 144 of the fibers. The total bundle denier was approximately 39 kilograms per 9000 meters. The bundle was twisted to 50 turns per meter using conventional ring twister equipment. The twisted bundle was feed into a draw line via quintet roller stand at feed speed of 10 meters per minute (mpm). The bundle then traversed through two bars submerged in water bath having length of 150 centimeters long. The two bars were located at approximately 130 centimeters from the water bath entrance. The bundle traversed through the bars such that the bundle followed a 180-degree turn (s-wrap) before exiting the water bath. The second bar the bundle contacted was heated to an indicated temperature of 38° C. The water bath temperature was 5° C. The bundle take-up speed was 57 meters per minute giving a draw ratio of 5.7. The fiber density was 0.77±0.02 grams per cubic centimeters.

Example 3

Fibers were formed as described in Example 2, except that the second bar heater was turned off. The fiber density was 0.71±0.02 grams per cubic centimeters.

Example 4

Fibers were formed as described in Example 2, except that the take-up speed was 59 meters per minute giving a draw ratio of 5.9. The fiber density was 0.69±0.03 grams per cubic centimeters.

Example 5

Fibers were formed as described in Example 4, except that the indicated second bar temperature was 20° C. and the take-up speed was 57 meters per minute giving a draw ratio of 5.7. The fiber density was 0.72±0.03 grams per cubic centimeters.

Example 6

Bicomponent fibers were formed that contained a core formed from a blend of 93 wt. % isotactic polypropylene (M3661 Total Petrochemicals) and 7 wt. % LOTADER® AX8900 (Arkema), and a sheath formed from 100 wt. % ASPUN™ 6835A (LLDPE, from Dow Chemical). The core was 70 vol. % of the fiber and the sheath was 30 vol. %. A bundle was formed that contained 288 of the fibers. The bundle was approximately 78 kilograms per 9000 meters. The bundle was feed into a water bath at 9° C. at 10 meters per minute using set of 5 rollers. The bundle traversed through draw bars (s-wrap) submerged under water at angle greater than 180-degrees. The draw bars where attached to a drive such that the rotational speed was control to 10 meters per minute. The bars were located at about 127 centimeters from the entrance of the bath. The total length of the water bath was 150 centimeters. The bundle was taken-up at speed of 53 meters per minute giving a draw ratio of 5.3. The density of the fiber was 0.81±0.02 grams per cubic centimeters.

Example 7

Fibers were formed as described in Example 6, except that the take-up speed was 57 meters per minute giving a draw ratio of 5.7. The density of the fiber was 0.71±0.02 grams per cubic centimeters.

Example 8

Fibers were formed as described in Example 6, except that, except feed speed was 20 meters per minute, the draw bar speed was 20 meters per minute, and the take-up speed was 106 meters per minute giving a draw ratio of 5.3. The density of the fiber was 0.76±0.03 grams per cubic centimeters.

Example 9

Fibers were formed as described in Example 8, except that, except take-up speed was 114 meters per minute giving a draw ratio of 5.7. The density of the fiber was 0.696±0.04 grams per cubic centimeters.

Example 10

Bicomponent fibers were formed contained a core formed from a blend of 93 wt. % semi-crystalline polyethylene terephthalate (PET 7200 Auriga) and 7 wt. % copolymer of ethylene and methyl acrylate containing 20% methyl acrylate content (Elvaloy® 1820ac, DuPont) and a sheath formed from 100 wt. % semi-crystalline polyethylene terephthalate (PET 7200 Auriga). The core was 70 vol. % of the fiber and the sheath was 30 vol. %. A bundle was formed that contained 24 of the fibers. The total bundle denier was approximately 1023 grams per 9000 meters. The twisted bundle was feed into a draw line via quintet roller stand at feed speed of 10 meters per minute (mpm). The bundle then traversed through two bars submerged in water bath having length of 150 centimeters long. The two bars were located at approximately 87 centimeters from the water bath entrance. The bundle traversed through the bars such that the bundle followed a 180-degree turn (s-wrap) before exiting the water bath. The water bath temperature was 10° C. The bundle take-up speed was 42 meters per minute giving a draw ratio of 4.2. Limited fiber breaks were observed.

Example 11

Fibers were formed as described in Example 10, except that the distance from the bath entrance was 108 cm. A medium amount of fiber break were observed.

Example 12

Bicomponent fibers were formed contained a core formed from a blend of 93 wt. % semi-crystalline polyethylene terephthalate (PET 7200 Auriga) and 7 wt. % copolymer of ethylene and methyl acrylate containing 20% methyl acrylate content (Elvaloy® 1820ac, DuPont) and a sheath formed from 100 wt. % semi-crystalline polyethylene terephthalate (PET 7200 Auriga). The core was 50 vol. % of the fiber and the sheath was 50 vol. %. A bundle was formed that contained 24 of the fibers. The total bundle denier was approximately 1023 grams per 9000 meters. The bundle was feed into a draw line via quintet roller stand at feed speed of 10 meters per minute (mpm). The bundle then traversed through two bars submerged in water bath having length of 150 centimeters long. The two bars were located at approximately 129 centimeters from the water bath entrance. The bundle traversed through the bars such that the bundle followed a 180-degree turn (s-wrap) before exiting the water bath. The water bath temperature was 10° C. The bundle take-up speed was 35 meters per minute giving a draw ratio of 3.5. A medium level of fiber breaks were observed.

Example 13

Fibers were formed as described in Example 12, except that the water bath temperature was 20° C. No fiber breaks were observed.

Example 14

Fibers were formed as described in Example 13, except that the take-up speed was 40 meters per minute giving a draw ratio of 4.0. Minimal breakage was observed.

Example 15

Fibers were formed as described in Example 13, except that the take up speed was 45 meters per minute giving a draw ratio of 4.5. Medium fiber breakage was observed.

Example 16

Monocomponent fibers were formed from a blend a blend of 93 wt. % semi-crystalline polyethylene terephthalate (PET 7200 Auriga) and 7 wt. % copolymer of ethylene and methyl acrylate containing 20% methyl acrylate content (Elvaloy® 1820ac, DuPont) A bundle was formed that contained 24 of the fibers. The bundle was approximately 1069 grams per 9000 meters. The bundle was feed into a draw line via quintet roller stand at feed speed of 10 meters per minute (mpm). The bundle then traversed through two bars submerged in water bath having length of 150 centimeters long. The two bars were located at approximately 129 centimeters from the water bath entrance. The bundle traversed through the bars such that the bundle followed a 180-degree turn (s-wrap) before exiting the water bath. The water bath temperature was 10° C. The bundle take-up speed was 35 meters per minute giving a draw ratio of 3.5. A high level of fiber breakage was observed.

Example 17

Monocomponent control fibers were formed from 100 wt. % semi-crystalline polyethylene terephthalate (PET 7200 Auriga). A bundle was formed that contained 24 of the fibers. The bundle was approximately 1105 grams per 9000 meters. The bundle was feed into a draw line via quintet roller stand at feed speed of 10 meters per minute (mpm). The bundle then traversed through two bars submerged in water bath having length of 150 centimeters long. The two bars were located at approximately 129 centimeters from the water bath entrance. The bundle traversed through the bars such that the bundle followed a 180-degree turn (s-wrap) before exiting the water bath. The water bath temperature was 10° C. The bundle take-up speed was 35 meters per minute giving a draw ratio of 3.0. All fibers were observed to break.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method for forming porous fibers, the method comprising:
supplying a bundle of fibers to a drawing system that includes at least one draw bar in contact with a fluidic medium having a temperature that is lower than the melting temperature of the matrix polymer, wherein at least a portion of the fibers are formed from a thermoplastic composition containing a continuous phase that includes a matrix polymer and a nanoinclusion additive dispersed within the continuous phase in the form of discrete domains; and
traversing the bundle of fibers over the draw bar, thereby forming a porous network in the fibers that includes a plurality of nanopores, optionally having an average cross-sectional dimension of about 800 nanometers or less.

2. The method of claim 1, wherein the draw bar is submerged within the fluidic medium, such as water.

3. The method of claim 1, wherein the fluidic medium is at a temperature of from about −20° C. to about 90° C.

4. The method of claim 1, wherein the width of the draw bar is from about 1 to about 50 millimeters.

5. The method of claim 1, wherein the draw bar is provided with at least one groove that is oriented in a direction generally parallel with a longitudinal direction of the fiber bundle.

6. The method of claim 1, wherein the draw bar is heated to a temperature that is greater than the temperature of the fluidic medium.

7. The method of claim 1, wherein the drawing system contains a chamber within which the fluidic medium is disposed, the draw bar being positioned within the chamber.

8. The method of claim 7, wherein the chamber defines an entrance and an exit and wherein the fiber bundle is supplied to the entrance of the chamber.

9. The method of claim 7, wherein the length of the chamber ranges from about 10 to about 800 centimeters.

10. The method of claim 7, wherein the bundle of fibers is in contact with the fluidic medium for a certain distance prior to traversing over the draw bar.

11. The method of claim 10, wherein the distance is from about 6 to about 600 centimeters.

12. The method of claim 1, wherein the drawing system contains a first draw bar and a second bar, wherein the bundle of fibers traverses sequentially over the first draw bar and then the second draw bar.

13. The method of claim 12, wherein the first and second draw bars are spaced apart by a distance between about 0.4 to about 50 millimeters.

14. The method of claim 12, wherein the first and second draw bars are positioned so that the fiber exits the second draw bar at an angle that is approximately 180° relative to the fiber bundle upon initial contact with the first draw bar.

15. The method of claim 1, wherein the bundle of fibers is drawn at a ratio of from about 1.1 to about 25.

16. The method of claim 1, wherein the method comprises:
supplying the bundle of fibers to a first stage of the drawing system that includes a first draw bar in contact with a fluidic medium having a first temperature;
thereafter, supplying the bundle of fibers to a second stage of the drawing system that includes a second draw bar in contact with a second fluidic medium having a second temperature;
wherein the first and second temperatures are lower than the melting temperature of the matrix polymer, and further wherein the second temperature is lower than the first temperature.

17. The method of claim 1, wherein the bundle contains about 5 or more fibers.

18. The method of claim 1, wherein the matrix polymer is a polyester, a polyolefin such as a substantially isotactic polypropylene homopolymer or a copolymer containing at least about 90% by weight propylene, or a combination thereof.

19. The method of claim 1, wherein the nanoinclusion additive includes a functionalized polyolefin, such as a polyepoxide.

20. The method of claim 1, wherein the composition further comprises a microinclusion additive dispersed within the continuous phase in the form of discrete domains, wherein the microinclusion additive optionally contains a polymer having a glass transition temperature of about 0° C. or more, such as polylactic acid.

21. The method of claim 1, wherein the porous network further includes micropores.

* * * * *